US011819275B2

(12) United States Patent
Tanaka et al.

(10) Patent No.: US 11,819,275 B2
(45) Date of Patent: Nov. 21, 2023

(54) OPTICAL COHERENCE TOMOGRAPHY APPARATUS, CONTROL METHOD FOR OPTICAL COHERENCE TOMOGRAPHY APPARATUS, AND COMPUTER-READABLE STORAGE MEDIUM

(71) Applicant: CANON KABUSHIKI KAISHA, Tokyo (JP)

(72) Inventors: Kazumasa Tanaka, Tokyo (JP); Hiroki Uchida, Tokyo (JP); Yoshihiko Iwase, Kanagawa (JP); Osamu Sagano, Tokyo (JP); Ritsuya Tomita, Kanagawa (JP)

(73) Assignee: Canon Kabushiki Kaisha, Tokyo (JP)

(*) Notice: Subject to any disclaimer, the term of this patent is extended or adjusted under 35 U.S.C. 154(b) by 42 days.

(21) Appl. No.: 17/546,084

(22) Filed: Dec. 9, 2021

(65) Prior Publication Data

US 2022/0183551 A1 Jun. 16, 2022

(30) Foreign Application Priority Data

Dec. 16, 2020 (JP) ................................ 2020-208772
Jun. 30, 2021 (JP) ................................ 2021-109337

(51) Int. Cl.
*G01B 9/02* (2022.01)
*A61B 3/10* (2006.01)
(Continued)

(52) U.S. Cl.
CPC ............ *A61B 3/102* (2013.01); *A61B 5/0066* (2013.01); *G01B 9/02091* (2013.01)

(58) Field of Classification Search
CPC .. A61B 3/102; A61B 5/0066; G01B 9/02091; G01B 9/0209; G01B 9/02064; G01B 9/02067; G06N 20/00
See application file for complete search history.

(56) References Cited

U.S. PATENT DOCUMENTS 7,643,154 B2 1/2010 Kikawa et al.
8,556,424 B2 10/2013 Iwase et al.
(Continued)

FOREIGN PATENT DOCUMENTS

JP 2008-154939 A 7/2008
JP 2020058800 A * 4/2020 ........... A61B 3/0025
(Continued)

*Primary Examiner* — Uzma Alam
*Assistant Examiner* — Jonathon Cook
(74) *Attorney, Agent, or Firm* — Venable LLP

(57) ABSTRACT

The optical coherence tomography apparatus is an optical coherence tomography apparatus that obtains a tomographic image of an eye to be examined by using combined light obtained by combining (a) return light from the eye to be examined irradiated with measurement light and (b) reference light, the optical coherence tomography apparatus including an optical path length difference changing unit arranged to change an optical path length difference between the measurement light and the reference light, a driving unit arranged to drive the optical path length difference changing unit, a determining unit configured to determine, using a learned model, a driving amount of the driving unit from the obtained tomographic image, and a controlling unit configured to control the driving unit using the determined driving amount.

28 Claims, 18 Drawing Sheets

(51) Int. Cl.
*G01B 9/02091* (2022.01)
*A61B 5/00* (2006.01)

(56) References Cited

U.S. PATENT DOCUMENTS

| | | | | |
|---|---|---|---|---|
| 8,634,081 | B2 | 1/2014 | Suehira et al. | |
| 8,657,440 | B2 | 2/2014 | Iwase et al. | |
| 8,845,098 | B2 | 9/2014 | Uchida | |
| 9,004,685 | B2 | 4/2015 | Iwase et al. | |
| 9,022,569 | B2 | 5/2015 | Nakahara et al. | |
| 9,025,844 | B2 | 5/2015 | Iwase et al. | |
| 9,042,622 | B2 | 5/2015 | Uchida | |
| 10,383,511 | B2 | 8/2019 | Iwase et al. | |
| 10,555,668 | B2 | 2/2020 | Fukuhara et al. | |
| 10,973,406 | B2 | 4/2021 | Imamura et al. | |
| 2008/0151256 | A1 | 6/2008 | Kikawa et al. | |
| 2009/0268020 | A1* | 10/2009 | Buckland | G01B 9/02064 348/78 |
| 2011/0137157 | A1 | 6/2011 | Imamura et al. | |
| 2014/0132923 | A1 | 5/2014 | Kawase et al. | |
| 2014/0132924 | A1 | 5/2014 | Sagano et al. | |
| 2018/0000341 | A1 | 1/2018 | Tomatsu et al. | |
| 2018/0344150 | A1 | 12/2018 | Bajraszewski et al. | |

FOREIGN PATENT DOCUMENTS

| | | | | | |
|---|---|---|---|---|---|
| WO | WO-2020075719 | A1 * | 4/2020 | | A61B 3/0025 |
| WO | WO-2020138128 | A1 * | 7/2020 | | G06N 3/04 |

* cited by examiner (a) (b) (c) (d) (e)

(a) (b) (c) (d) (e) (f)

(a) (b) (c) (d)

(a)

(b)

(a)

(b)

OPTICAL COHERENCE TOMOGRAPHY APPARATUS, CONTROL METHOD FOR OPTICAL COHERENCE TOMOGRAPHY APPARATUS, AND COMPUTER-READABLE STORAGE MEDIUM

BACKGROUND

Field of the Disclosure

The disclosure according to the present specification relates to an optical coherence tomography apparatus, a control method for an optical coherence tomography apparatus, and a computer-readable storage medium.

Description of the Related Art

Apparatuses for optical coherence tomography (OCT), which uses interference between low coherence light beams to obtain a tomographic image, (OCT apparatuses) have been in practical use. The OCT apparatuses can obtain a tomographic image at a resolution on the order of a wavelength of light entering an object to be examined, and thus the tomographic image of the object to be examined can be obtained at a high resolution. The OCT apparatuses are useful as ophthalmological apparatuses for obtaining a tomographic image particularly of a retina located at a fundus.

A configuration of OCT is, for example, time domain OCT (TD-OCT), which is a combination of a wide-band light source and a Michelson interferometer. This is configured such that a coherence gate on which a reference mirror is mounted is driven at a constant speed, and light interfered with backscattered light obtained by a measurement arm is measured, by which a reflected light intensity distribution in a depth direction is obtained. It is however difficult for such TD-OCT to obtain an image at high speed because the TD-OCT requires mechanical scanning. Hence, spectral domain OCT (SD-OCT), which uses a wide-band light source and obtains an interference signal with a spectroscope, and swept source OCT (SS-OCT), which uses a high-speed wavelength-sweeping light source to perform spectroscopy with time, have been developed as a method for obtaining an image at higher speed, which have enabled tomographic images of wider angles of view to be obtained.

Such OCT apparatuses detect an interference signal of measurement light applied to an eye to be examined and reference light applied to a reference mirror. To image an eyes to be examined with an OCT apparatus, an optical path length difference between the measurement light and the reference light needs to be adjusted with accuracy. In this regard, Japanese Patent Application Laid-Open No. 2008-154939 describes an optical image measurement apparatus that determines a position of a retina in a tomographic image and adjusts an optical path length difference between measurement light and reference light based on the determined position so that the retina is located at a predetermined position.

A method for adjusting an optical path length difference between measurement light and reference light based on a position of a retina determined in a tomographic image involves a problem in that the adjustment may not be performed accurately depending on a shape of an eye to be examined. For example, in a case where a retina has a large bend due to myopia, a peripheral portion of the retina may protrude from a tomographic image to disappear or may be displayed being turned up or down even when a center portion of the retina is aligned with a position in the tomographic image that allows observation (predetermined position). This problem appears prominently particularly in an OCT apparatus having a wide imaging view angle.

SUMMARY

Hence, an objective of the disclosure of the present specification is to adjust, in optical coherence tomography, an optical path length difference between measurement light and reference light with high accuracy.

An optical coherence tomography apparatus according to an embodiment of the disclosure of the present specification is an optical coherence tomography apparatus that obtains a tomographic image of an eye to be examined by using combined light obtained by combining (a) return light from the eye to be examined irradiated with measurement light and (b) reference light, the optical coherence tomography apparatus including an optical path length difference changing unit arranged to change an optical path length difference between the measurement light and the reference light, a driving unit arranged to drive the optical path length difference changing unit, a determining unit configured to determine, using a learned model, a driving amount of the driving unit from the obtained tomographic image, and a controlling unit configured to control the driving unit using the determined driving amount.

Further features of the present invention will become apparent from the following description of exemplary embodiments with reference to the attached drawings.

DESCRIPTION OF THE EMBODIMENTS

Figure 1:
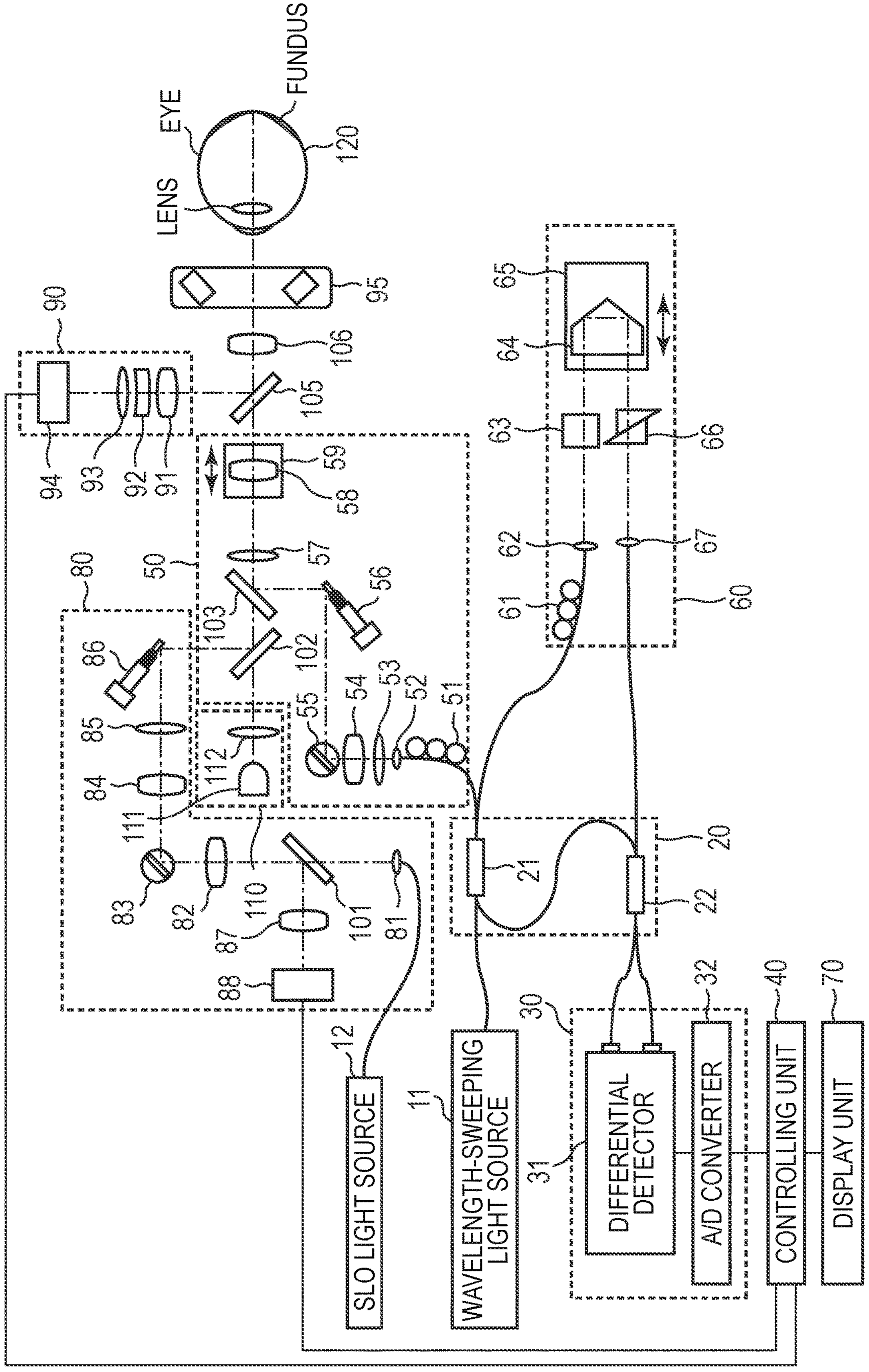
FIG. 1 illustrates an example of a schematic configuration of an optical coherence tomography apparatus according to Embodiment 1.

Preferred embodiments of the present invention will now be described in detail in accordance with the accompanying drawings.

Note that dimensions, materials, shapes, relative positions of constituent components, and the like to be described in the following embodiments are optional and can be modified in conformance with a configuration of or various conditions for an apparatus to which the present disclosure is to be applied. In addition, the same reference characters will be used in the drawings for indicating the same elements or functionally similar elements. Note that constituent components, members, and part of processing in the drawings that are not important in describing may not be illustrated.

Note that a machine learning model herein refers to a learning model provided by a machine learning algorithm. Concrete algorithms for machine learning include those for nearest neighbor methods, naive Bayes methods, decision trees, support vector machines. The algorithms also include those for deep learning, which uses a neural network to generate feature quantities for learning and connection weight coefficients on its own. In addition, examples of an algorithm using a decision tree include those for methods using gradient boosting, such as LightGBM and XGBoost. Of the algorithms described above, available one can be used and applied to the following embodiments and modifications as appropriate. Supervisory data refers to training data and includes a pair of input data and output data (ground truth).

A learned model refers to a model that is a machine learning model according to any machine learning algorithm such as deep learning and has been trained with appropriate supervisory data (training data) in advance. Although the learned model is obtained in advance by using the appropriate training data, a possibility of further training is not eliminated, and the learned model can be subjected to additional training. The additional training can be performed after the apparatus is installed at a service space.

Herein, a depth direction of a subject is defined as a Z direction, a direction perpendicular to the Z direction is defined as an X direction, and a direction perpendicular to the Z direction and the X direction is defined as a Y direction.

Embodiments 1 and 2 will be described below as exemplary embodiments. Embodiment 1 will describe an example of performing alignment processing on an optical path length difference changing unit with a learned model, and Embodiment 2 will describe an example of performing tracking processing on the optical path length difference changing unit with a learned model.

Embodiment 1

As an example of an ophthalmic photography apparatus according to Embodiment 1 of the present disclosure, an optical coherence tomography apparatus will be described below with reference to FIG. 1 to FIG. 12. The optical coherence tomography apparatus in the present embodiment has a configuration of SS-OCT. The configuration of the optical coherence tomography apparatus is however not limited to SS-OCT and may be of SD-OCT.

FIG. 1 is a diagram illustrating a configuration example of an optical coherence tomography apparatus (OCT apparatus) according to the present embodiment. The OCT apparatus includes a wavelength-sweeping light source 11 that sweeps a frequency of light emitted, an OCT interference unit 20 that generates interfered light, a detection unit 30 that detects the interfered light, and a controlling unit 40 that obtains, based on the interfered light, information on fundus of an eye to be examined being a subject 120. The OCT apparatus further includes a measurement arm 50 and a reference arm 60. Additionally, the OCT apparatus includes an SLO light source 12 for a scanning laser ophthalmoscope (SLO) and includes an SLO optical system 80 for obtaining reflected light from the fundus and an anterior ocular segment imaging unit 90.

<Configuration of OCT Measurement System>

The OCT interference unit 20 includes couplers 21 and 22. First, the coupler 21 splits light emitted from the wavelength-sweeping light source 11 into measurement light with which the fundus is to be irradiated and reference light. In the present embodiment, a split ratio is about 2:8, measurement light:reference light=2:8. Note that the split ratio may be set optionally according to a desired configuration.

The measurement light is applied to the fundus being the subject 120 via the measurement arm 50. More specifically, entering the measurement arm 50, the irradiation light is adjusted in its polarized state by a polarization controller 51 and then emitted as spatial light from a collimator 52. The irradiation light then passes through lenses 53 and 54, an X scanner 55, a Y scanner 56, a dichroic mirror 103, a lens 57, a focus lens 58, a dichroic mirror 105, and an objective lens 106 and is applied to the fundus of the subject 120.

The X scanner 55 and the Y scanner 56 are scanning units each having a function of scanning the fundus with the irradiation light. The scanning units change a position of irradiation of the fundus with the measurement light.

The dichroic mirror 103 has characteristics of reflecting light having wavelengths of 1000 nm to 1100 nm and allowing light of the other wavelengths to pass therethrough. The dichroic mirror 105 has characteristics of reflecting light having wavelengths of 820 nm to 920 nm and allowing light of the other wavelengths to pass therethrough.

The focus lens 58 is fixed to a focus stage 59 and is movable in an optical axis direction by drive of the focus stage 59 by the controlling unit 40. By moving the focus lens 58, a focal position of the measurement light can be changed.

Backscattered light (reflected light) from the fundus of the subject 120 travels along the above-described optical path again and is emitted from the measurement arm 50. The reflected light that has exited from the measurement arm 50 enters the coupler 22 via the coupler 21. According to the aforementioned split ratio of the coupler 21, 80% of the reflected light (return light from the fundus) that has passed through the coupler 21 is directed to the coupler 22.

Meanwhile, the reference light enters the coupler 22 via the reference arm 60. More specifically, entering the reference arm 60, the reference light is adjusted in its polarized state by a polarization controller 61 and then emitted as spatial light from a collimator 62. The reference light then passes through a dispersion compensation glass 63, a coherence gate 64, and a dispersion controlling prism pair 66, enters an optical fiber via a collimator lens 67, is emitted from the reference arm 60, and enters the coupler 22.

The coherence gate 64 is an example of an optical path length difference changing unit that changes a difference in optical path length between the measurement light and the reference light by changing an optical path length of the reference light. Note that the optical path length difference changing unit may be one that changes, for example, an optical path length of the measurement light. The coherence gate 64 includes, for example, a retroreflector prism. The coherence gate 64 may include at least two or more mirrors or may include a single mirror. The coherence gate 64 is capable of being driven in an optical axis direction by a driving motor 65. Note that the driving motor 65 is an example of a driving unit that drives the optical path length difference changing unit and may include any known motor such as a stepping motor and a DC motor. In addition to the driving motor 65, the driving unit may include a stage or the like.

In the coupler 22, the reflected light from the subject 120 having passed through the measurement arm 50 interferes with the light having passed through the reference arm 60. The interfered light is detected by the detection unit 30. The detection unit 30 includes a differential detector 31 and an A/D converter 32.

Immediately after the interfered light is generated by the coupler 22, the interfered light is split into interfered light beams, and in the detection unit 30, the interfered light beams are detected by the differential detector 31 and converted into an OCT interference signal in a form of an electric signal. The A/D converter 32 converts the OCT interference signal in a form of an electric signal, which is converted into by the differential detector 31, into a digital signal. Here, in the OCT apparatus illustrated in FIG. 1, the interfered light beams are sampled for every optical frequency (wavenumber) based on a k-clock signal transmitted by a k-clock generating unit that is built in the wavelength-sweeping light source 11. The A/D converter 32 outputs the digital signal of the OCT interference signal converted into to the controlling unit 40. The controlling unit 40 is capable of obtaining, based on the digital signal of the OCT interference signal output from the A/D converter 32, information about a section of the subject 120 and generating a tomographic image.

The above is a process for obtaining information about a section of the subject 120 at one point of the subject 120, and obtaining information about a section of the subject 120 in a depth direction in this manner is called A-scan. In addition, obtaining information about a section of the subject 120 in a direction perpendicular to that of the A-scan, that is, information about a two-dimensional image, is called B-scan. Moreover, obtaining information about a section of the subject 120 in a direction perpendicular to scanning directions of both the A-scan and the B-scan is called C-scan. In a case where a two-dimensional raster scan is performed on a fundus to obtain a three-dimensional tomographic image, a scanning direction of a fast scan is called B-scan direction, and a scanning direction of a slow scan that is performed on B-scans arranged in a direction perpendicular to the B-scan direction is called C-scan direction. Performing an A-scan and a B-scan produces a two-dimensional tomographic image, and performing an A-scan, a B-scan, and a C-scan produces a three-dimensional tomographic image. The B-scan and the C-scan are performed by scanning the fundus with the measurement light by using the X scanner 55 and the Y scanner 56 described above.

Note that the X scanner 55 and the Y scanner 56 include respective deflection mirrors that are disposed such that rotation axes of the deflection mirrors are perpendicular to each other. The X scanner 55 performs a scan in an X-axis direction, and the Y scanner 56 performs a scan in a Y-axis direction. The X-axis direction and the Y-axis direction are both perpendicular to an eye axis direction of an eyeball and are perpendicular to each other. In addition, linear scan directions of the B-scan and the C-scan each may not match the X-axis direction or the Y-axis direction. For this reason, the linear scan directions of the B-scan and the C-scan can be determined as appropriate according to a two-dimensional tomographic image or three-dimensional tomographic image to be captured. In the present embodiment, the scanning unit of the OCT optical system includes the X scanner 55 and the Y scanner 56; however, the OCT optical system may include, for example, a MEMS mirror, which can deflect light in a direction in a two-dimensional manner singly.

<Configuration of SLO Measurement System>

The light that has exited from the SLO light source 12 is applied to the fundus via the SLO optical system 80. More specifically, the light that has entered the SLO optical system 80 is emitted as parallel rays into a space from a collimator 81. The light then passes through a hole portion of a hole mirror 101, via a lens 82, an X scanner 83, lenses 84 and 85, and a Y scanner 86, reaches a dichroic mirror 102, and is reflected by the dichroic mirror 102. The X scanner 83 and the Y scanner 86 are an example of a scanning unit for SLO. The scanning unit for SLO may include the X scanner 55 and the Y scanner 56 for OCT as an XY scanning unit shared by the SLO optical system 80 and the OCT optical system. The dichroic mirror 102 has characteristics of reflecting light having wavelengths of 760 nm to 800 nm and allowing light of the other wavelengths to pass therethrough. The light reflected by the dichroic mirror 102 passes along the same optical path as the optical path of the measurement light for OCT and reaches the fundus of the subject 120.

The measurement light for SLO applied to the fundus is reflected and scattered by the fundus, travels along the above-described optical path, reaches the hole mirror 101, and is reflected by the hole mirror 101. The light reflected by the hole mirror 101 passes through a lens 87 and received by an avalanche photodiode (hereinafter, abbreviated as APD) 88, where the light is converted into an electric signal and output to the controlling unit 40. The controlling unit 40 is capable of generating, based on an SLO fundus signal output from the APD 88, an SLO image, which is a fundus front image. Note that the signal output from the APD 88 may be output to the controlling unit 40 in a form of a digital signal by an A/D converter not illustrated.

Here, a position of the hole mirror 101 is conjugate to a pupil position of the eye to be examined. As a result, regarding the measurement light for SLO applied to the fundus, light that passed through a peripheral portion of the pupil out of the light having been reflected and scattered by the fundus is reflected by the hole mirror 101.

In the present embodiment, the OCT apparatus includes the SLO optical system 80 as a configuration for obtaining a fundus front image, which however does not limit the configuration for obtaining a fundus front image. For example, the OCT apparatus may include a fundus photography system for obtaining a fundus photograph, and hereafter, processing with an SLO image may be substituted by processing with a fundus photograph.

<Configuration of Anterior Ocular Segment Measurement System>

The anterior ocular segment imaging unit 90 is used for imaging an anterior ocular segment of the subject 120 with an illumination light source 95 that includes an LED emitting illumination light having a wavelength of 860 nm. The illumination light emitted from the illumination light source 95 is reflected by the anterior ocular segment, passes through the objective lens 106, and reaches the dichroic mirror 105. The light reflected by the dichroic mirror 105 passes through lenses 91, 92 and 93 and is received by an anterior segment camera 94. The light received by the anterior segment camera 94 is converted into an electric signal and output to the controlling unit 40. The controlling unit 40 is capable of generating an anterior segment image based on the signal output from the anterior segment camera 94. Note that the signal output from the anterior segment camera 94 may be output to the controlling unit 40 in a form of a digital signal by an A/D converter not illustrated.

<Internal Fixation Lamp 110>

An internal fixation lamp 110 includes a display unit 111 for the internal fixation lamp and a lens 112. In the present embodiment, as the display unit 111 for the internal fixation lamp, one in which a plurality of light emitting diodes (LEDs) is arranged in a matrix pattern is used. Lighting positions of the light emitting diodes are changed depending on a region to be imaged. Light from the display unit 111 for the internal fixation lamp passes through the lens 112 and is directed to the subject 120. Note that the light that has exited from the display unit 111 for the internal fixation lamp has a wavelength of 520 nm, and on the display unit 111 for the internal fixation lamp, a desired preset pattern is displayed.

<Controlling Unit 40>

The controlling unit 40 performs signal processing on the OCT interference signal converted into a digital signal to perform various types of image processing such as generating an optical coherence tomographic image. Likewise, the controlling unit 40 is capable of processing the SLO fundus signal output from the APD 88 to generate an SLO image. In addition, the controlling unit 40 is capable of processing the signal output from the anterior segment camera 94 to generate an anterior segment image.

Based on a program, the controlling unit 40 controls drive mechanisms in the OCT apparatus including the driving motor 65 for the coherence gate 64. The controlling unit 40 therefore functions as an example of a controlling unit that controls the driving unit.

The controlling unit 40 may be a computer built in (inside) the OCT apparatus or may be a separate (outside) computer to which the OCT apparatus is connected so as to be able to communicate with the computer. The controlling unit 40 may be, for example, a personal computer (PC); a desktop PC, a laptop PC, a tablet PC (portable information terminal) may be used. At this time, a communication connection between the controlling unit 40 and the ophthalmological equipment may be a connection made by wired communication or a connection made by wireless communication. Note that a processor of the computer may be a central processing unit (CPU). The processor may be, for example, a micro processing unit (MPU), a graphical processing unit (GPU), or a field-programmable gate array (FPGA).

<Adjustment Flow>

Figure 2:
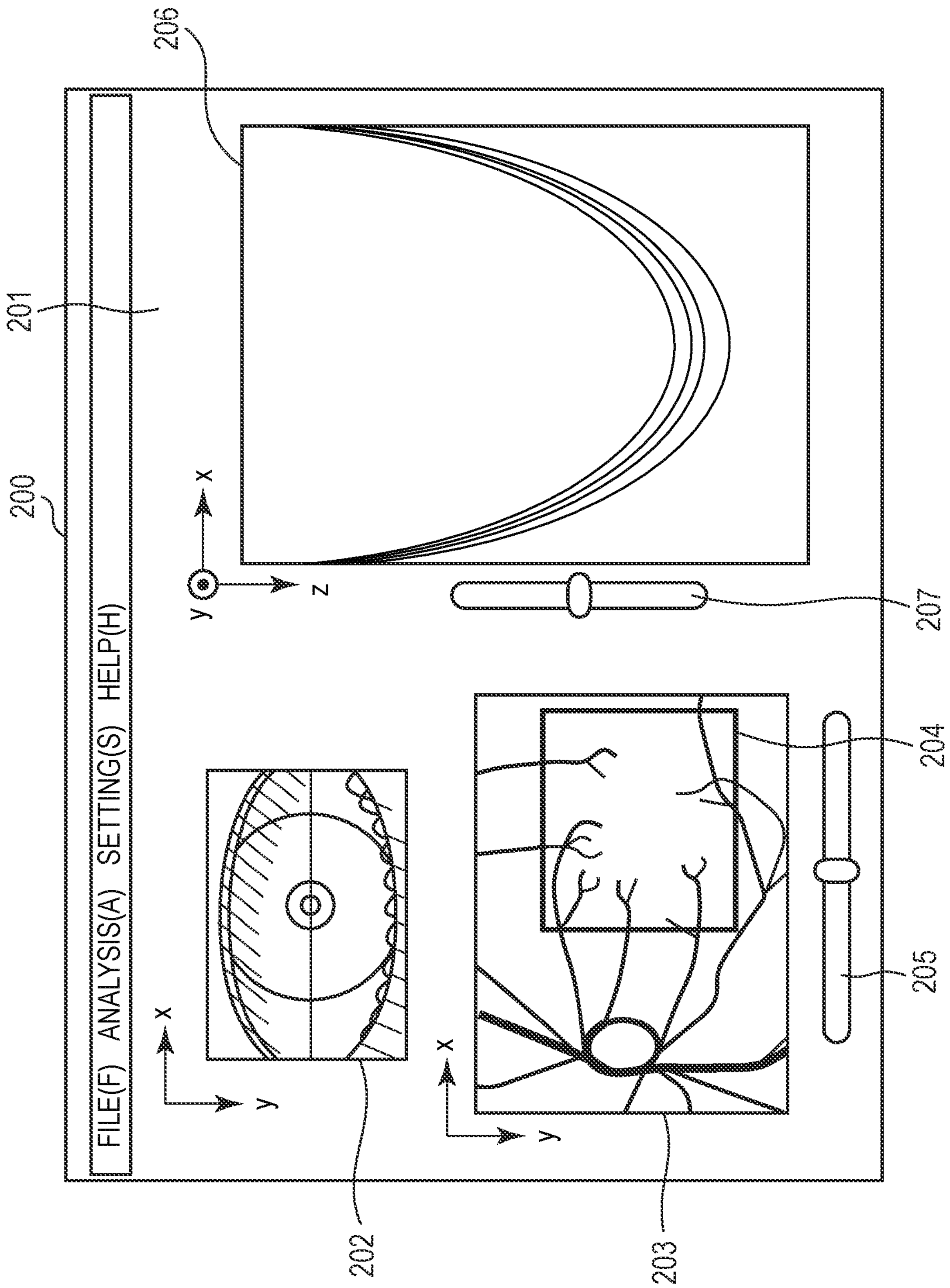
FIG. 2 illustrates an example of an imaging screen according to Embodiment 1.

Information on the fundus and the anterior ocular segment obtained as results of the signal processing by the controlling unit 40 is displayed by a display unit 70. FIG. 2 illustrates an example of an imaging screen 200 displayed on the display unit 70 at the time of imaging. In a display region 201 as an example of a display region of the imaging screen

200, an anterior segment image 202, an SLO image 203, and a tomographic image 206, which are generated by the controlling unit 40, are displayed.

With reference to the imaging screen 200 illustrated in FIG. 2, a procedure of an adjustment process such as adjusting alignment for imaging with the OCT apparatus will be described below. First, based on the anterior segment image 202, alignment of the measurement light of the OCT apparatus with the subject 120 in the optical axis direction is adjusted. The alignment may be adjusted manually by an examiner or may be adjusted automatically by the controlling unit 40 recognizing an image of the anterior segment image 202.

Next, focus adjustment is performed so that the SLO image 203 becomes optimum. The focus adjustment may be performed manually by the examiner with a focus adjuster 205 or may be performed automatically by the controlling unit 40 based on the SLO image 203. In a case where the focus adjuster 205 is used, the controlling unit 40 drives the focus stage 59 correspondingly to an operation of the focus adjuster 205 by the examiner, moving the focus lens 58.

Next, an OCT scan area is set. The OCT scan area can be specified with, for example, a guide 204 displayed on the SLO image 203. The guide can be set to have any size and shape and to be at any position; for example, a 23 mm×20 mm quadrilateral, a radial pattern inscribed in a circle having a diameter of 10 mm, a 10-mm line pattern can be selected as the guide. The controlling unit 40 causes the display unit 70 to display, as the tomographic image 206, a given tomographic image that is obtained within the scan area specified with the guide 204.

Lastly, positional adjustment (alignment) of the coherence gate 64 is performed such that the tomographic image 206 becomes optimum. An optimal position for the coherence gate 64 differs between a vitreous body mode, which uses a normal image in which a DC component of the interference signal appears in an upper part of a tomographic image, and a choroid mode, which uses a reverse image in which the DC components appear in a lower part of a tomographic image. Due to characteristics of coherence, in the vitreous body mode, the tomographic image is seen brighter at an upper part of the image, which is favorable for observing particularly a region on a vitreous body side of a retina. In contrast, in the choroid mode, the tomographic image is seen brighter at a lower part of the image, which is favorable for observing particularly a region on a choroid side of the retina. For each imaging, the examiner can specify one of the vitreous body mode and the choroid mode on the imaging screen or the like. Alternatively, before imaging, the examiner may set one of the vitreous body mode and the choroid mode together with an imaging condition such as a scan angle. A position of the coherence gate 64 is adjusted based on whether the mode is the vitreous body mode or the choroid mode.

Figure 3:
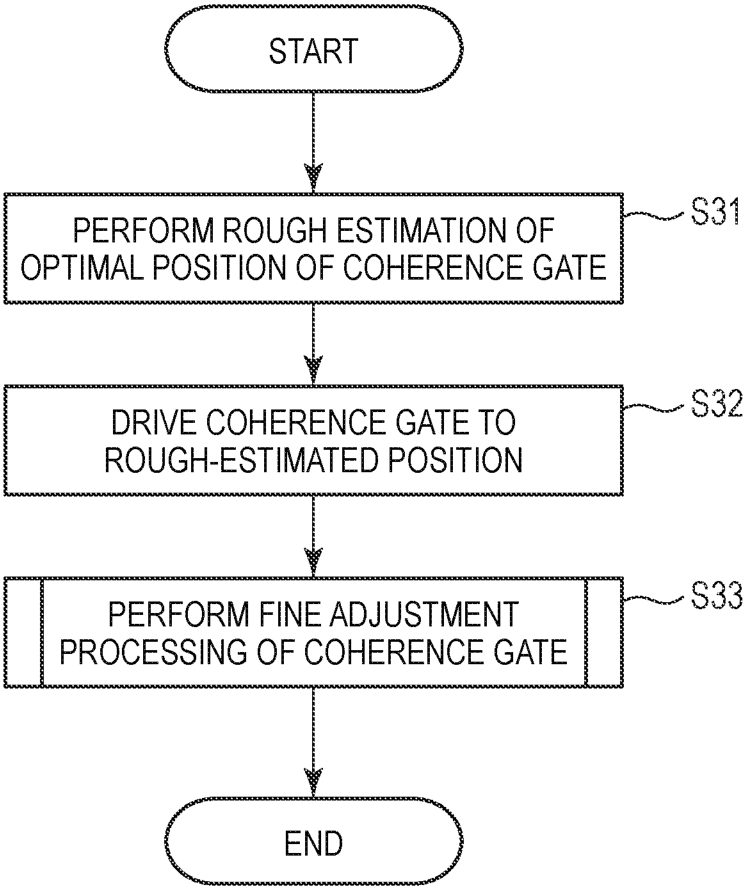
FIG. 3 illustrates an example of a flowchart of position adjustment processing of a coherence gate according to Embodiment 1.

With reference to FIG. 3, position adjustment processing of the coherence gate 64 according to the present embodiment will be described below for each step. FIG. 3 is a flowchart illustrating operations in the position adjustment processing of the coherence gate according to the present embodiment.

As the position adjustment processing of the coherence gate is started, the processing proceeds to step S31. In step S31, the controlling unit 40 roughly estimates an optimal position (target position) for the coherence gate 64 (rough estimation) based on a result of focus adjustment with the SLO image 203. The rough estimation is performed by, for example, using a conversion formula that is obtained by conducting regression analysis of relations between results of focus adjustment using SLO images performed on many eyes to be examined and optimal positions of the coherence gate 64. By performing such a process, the optimal position for the coherence gate 64 can be roughly estimated because there is a correlation between a diopter scale of an eye to be examined and an optimal position for the coherence gate 64. Note that how to perform the rough estimation is not limited to this; for example, the rough estimation may be performed based on a result of focus adjustment with the anterior segment image 202. Alternatively, for example, the rough estimation may be performed based on a result of obtaining a fundus photograph and performing focus adjustment by an image plane phase difference method or the like. Alternatively, the rough estimation may be performed by substituting an initial set value for any one of various types of focusing into the conversion formula. As the initial set value used here, a representative value such as a focus value optically calculated for an average eye to be examined and an average value resulting from focus adjustment performed on many eyes to be examined can be used. The optimal position roughly estimated will be hereinafter called a rough-estimated position. The rough-estimated position may be a representative value such as a position of the coherence gate 64 optically calculated for an average eye to be examined and an average value resulting from adjustments of the coherence gate 64 performed on many eyes to be examined can be used.

In step S32, the controlling unit 40 drives the coherence gate 64 from an initial position of the coherence gate 64 to the rough-estimated position. The initial position of the coherence gate 64 may be an end of a range within which the coherence gate 64 can be driven. Alternatively, the initial position may be a center position of the range within which the coherence gate 64 can be driven, a position resulting from adjustments of the coherence gate 64 in past examinations, or any other position. Here, a driving speed of the coherence gate 64 may be set at a possible maximum speed. A tomographic image obtained when the coherence gate 64 is moved to the rough-estimated position may be an image obtained by a B-scan (B-scan image) at an observation target position or may be a B-scan image at a representative position such that a position that lies at a center of an imaging view angle.

Figure 4:
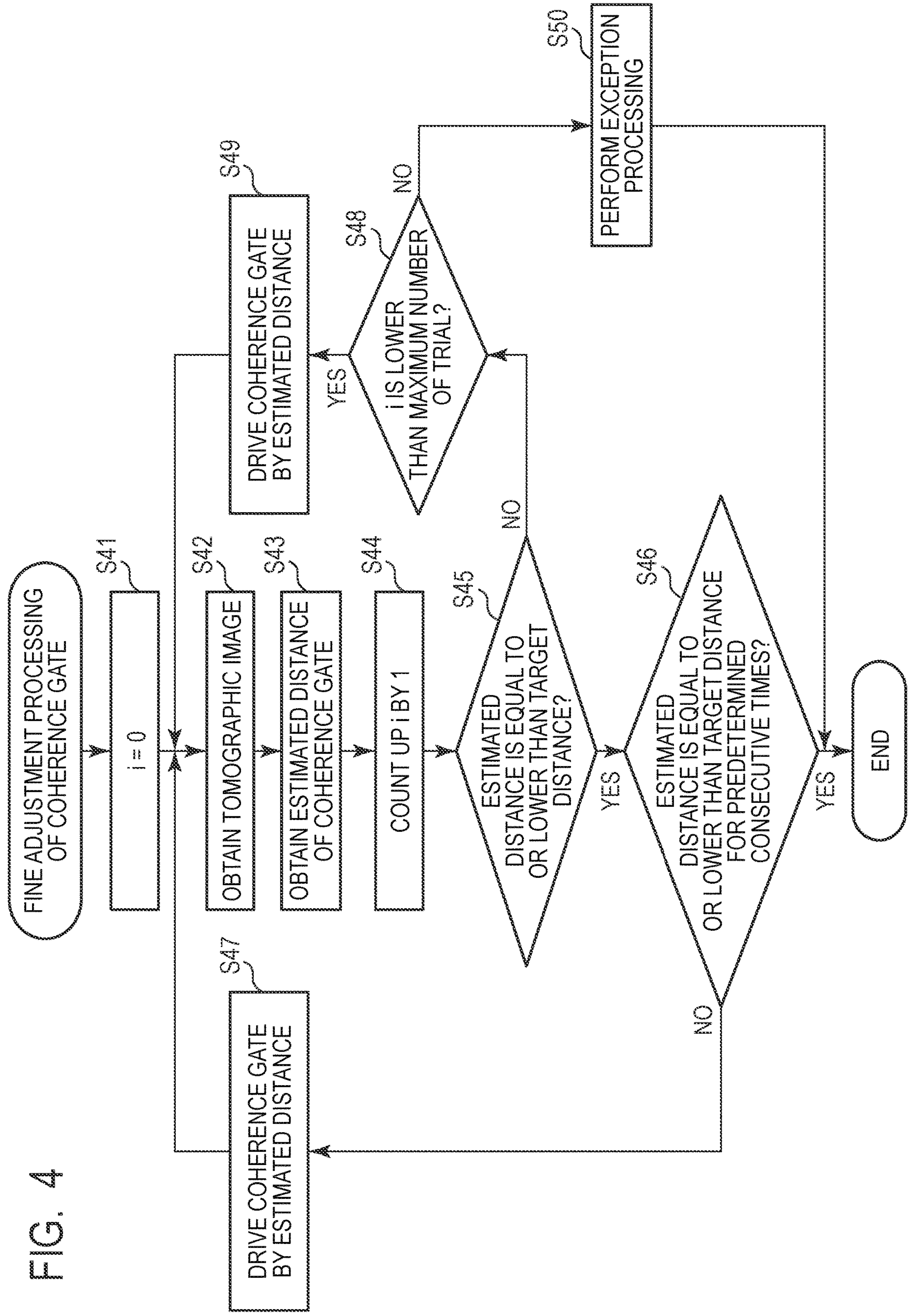
FIG. 4 illustrates an example of a flowchart of fine adjustment processing of coherence gate according to Embodiment 1.

Next, in step S33, the controlling unit 40 performs fine adjustment on the position of the coherence gate 64. With reference to FIG. 4, fine adjustment processing of coherence gate in the present embodiment will be described. The following fine adjustment processing of coherence gate is performed by the controlling unit 40.

As the fine adjustment processing of coherence gate is started, the processing proceeds to step S41. In step S41, the controlling unit 40 sets a number i of trials at zero.

Next, in step S42, the controlling unit 40 obtains a tomographic image. The tomographic image obtained here may be a B-scan image at a specific, designated XY position or may be a B-scan image at a representative XY position such as one that lies on a center line of (line passing a center of) an imaging view angle. The tomographic image obtained in the adjustment processing will be hereinafter called preview image. The preview image may be a low-resolution image generated by dropping data from a tomographic image obtained by imaging.

The controlling unit 40 determines an image quality of the tomographic image obtained in step S42, and when the image quality is lower than a threshold value, the controlling unit 40 may not use the tomographic image but may obtain a tomographic image of a next frame. This can prevent a malfunction caused by a blink of a subject that specifically darkens a tomographic image. As an evaluation index for the image quality, for example, an intensity value of the tomographic image in a given range can be used. Alternatively, a variance, a standard deviation, a skewness, a kurtosis, or the like of a frequency distribution (histogram distribution) of the image may be used as the evaluation index for the image quality. When the subject blinks, pixels having high intensity values are reduced, and thus these values vary. Using the frequency distribution for the evaluation index allows the image quality to be determined irrespective of a difference in brightness of the image as a whole.

Next, in step S43, the controlling unit 40 uses a learned model to obtain an estimated distance of the coherence gate 64 from the obtained tomographic image. The estimated distance here is an estimated distance from a current position to the optimal position for the coherence gate 64. The estimated distance is a signed value, and the sign indicates a direction of driving the coherence gate 64. Here, a process performed in step S43 will be described in detail by way of an example in which a neural network model is used as the learned model.

Figure 5:
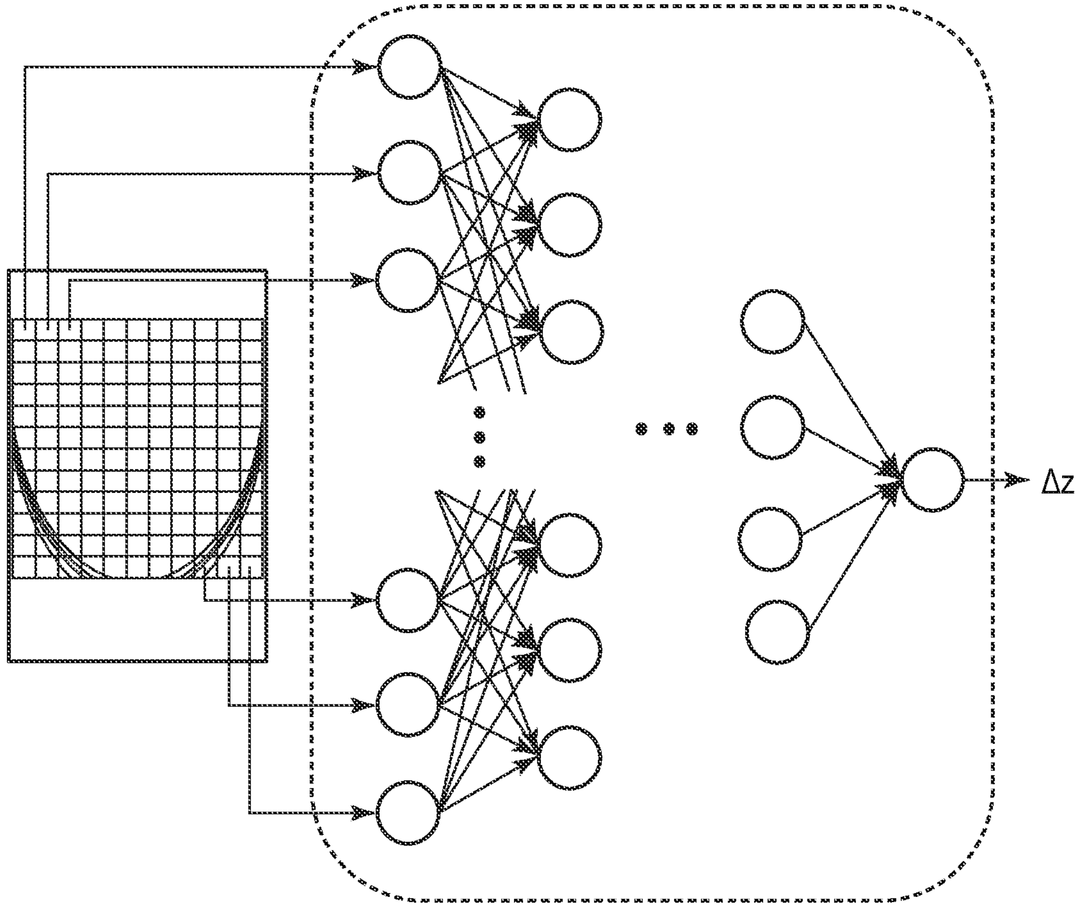
FIG. 5 illustrates an example of a schematic diagram of a neural network model according to Embodiment 1.

FIG. 5 illustrates an example of a schematic diagram of a neural network model according to the present embodiment. According to the model schematic diagram illustrated in FIG. 5, the neural network is designed to output an estimated distance (a distance from a current position to an optimal position) Δz of the coherence gate 64 from image information that is input as two-dimensional pixel array data on a tomographic image. The estimated distance Δz to be output is based on content learned through a machine learning process (deep learning), and the neural network according to the present embodiment learns relations between information about shapes of retinae included in tomographic images and estimated distances Δz.

The model used in the present embodiment may be a regression model in which input data is a tomographic image and output data is an estimated distance of the coherence gate 64. The model used in the present embodiment may be a classification model in which input data is a tomographic image and output data is one of classes at a plurality of levels into which an estimated distance of the coherence gate 64 is divided.

Figure 10:
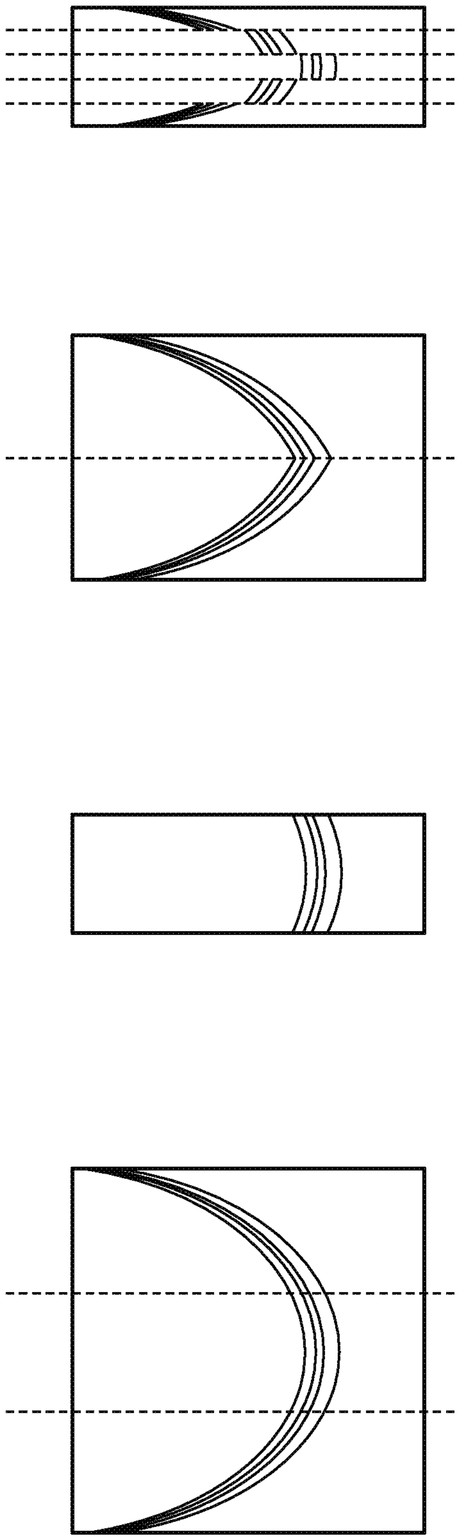
FIG. 10 illustrates an example of processing for extracting part of a tomographic image according to Embodiment 1.

The input data may be changed in size from that of a tomographic image obtained by the OCT apparatus in view of a load of the learning or the estimation. A method for changing the size may be a method in which, for example, the size is reduced by dropping an A-scan data item from the tomographic image every other A-scan data item or every plurality of A-scan data items. Alternatively, the method for changing the size may be a method in which the size is reduced by dropping data from each A-scan data item of the tomographic image. Alternatively, a region being part of the tomographic image may be extracted as illustrated in FIG. 10 to be described later. Note that the learned model used in the present embodiment is stored in the controlling unit 40.

The neural network according to the basic specifications described above can be configured as a convolutional neural network (CNN) which enables flexible pattern recognition, for example, by forming an intermediate layer after an input layer as a combination of what one calls a convolution layer and a pooling layer. In addition, for example, a layer closest to an output layer can be formed as a fully connected layer, which is suitable for optimum value operations.

The neural network according to the present embodiment can be trained by any one of what one calls supervised learning and reinforcement learning. Here, how to train the neural network according to the present embodiment will be described. An example of how the controlling unit 40 performs the training of the learned model will be described below, but note that the training may be performed by a training unit not illustrated separate from the controlling unit 40 or may be performed by a separate apparatus.

Figure 6:
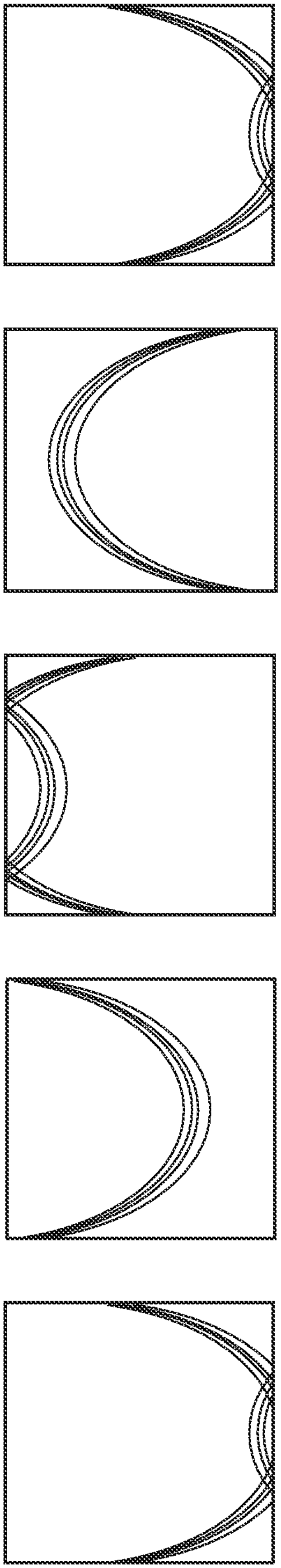
FIG. 6 illustrates an example of training data according to Embodiment 1.

In a case where the supervised learning is performed, tomographic images can be used as input data, and estimated distances of the coherence gate 64 can be used as output data. With reference to FIG. 6, training data for performing the supervised learning will be described below. FIG. 6 is a diagram for describing tomographic images used for the learning and illustrates an example of tomographic images of an eye to be examined that are obtained in a state where the coherence gate 64 is located at a plurality of positions.

The tomographic images illustrated as (a) to (e) in FIG. 6 can be obtained by, for example, sequentially recording the tomographic images and imaging time points of the tomographic images while the coherence gate 64 is driven across a range where the coherence gate 64 can be driven. The tomographic images and corresponding driving distances of the coherence gate 64 can be obtained in association with each other from a driving speed of the driving motor 65 for the coherence gate 64 and a time interval between every tomographic image obtaining. The driving speed of the driving motor 65 for the coherence gate 64 may be calculated, for example, in an averaging manner by dividing a distance from a driving start position to a driving end position by a driving duration.

The image (a) in FIG. 6 illustrates a case where a retina in the tomographic image deviates downward from an optimal position for the retina because the coherence gate 64 deviates from the optimal position for the coherence gate 64. Since the coherence gate 64 deviates from the optimal position, a center portion of the retina in the tomographic image is turned up. This is unsuitable for observation and diagnosis.

The image (b) in FIG. 6 illustrates an example of a tomographic image when the retina is located at the optimal position because the coherence gate 64 is driven in a direction that causes the retina to be seen in an upper part of the tomographic image than in the image (a) in FIG. 6. The optimal position for the coherence gate 64 that is a target for the adjustment of an optical path length difference between the measurement light and the reference light (target position) can be set or adjusted by an examiner so as to allow the entire retina to be seen in a tomographic image or so as to facilitate observation of a noteworthy region. In addition, in a case of imaging in the vitreous body mode, in which a DC component of an interference signal appears in an upper part of the tomographic image, an image corresponding to the interference signal is seen brighter at an upper part of the tomographic image. The optimal position for the coherence gate 64 thus may be at, for example, a position that causes the retina to be seen in the tomographic image at a part as up as possible to the extent that the retina is not turned down or, in view of the possibility that the coherence gate 64 could move from the position during imaging, a position that causes the retina to be seen lower than the part by a margin. In addition, at a peripheral portion outside a center portion of a bend of the retina, the retina is seen upper in the tomographic image than at the center portion of the bend of the retina. In view of this fact, in a case where the position of the coherence gate 64 is adjusted by referring to a tomographic image at the center portion of the bend of the retina, the optimal position for the coherence gate 64 may be set at a position that causes the retina to be seen lower by this margin. Alternatively, the optimal position may be set on a rule basis based on a representative point such as one in the center portion and one in the peripheral portion of the retina. At this time, a region having high viewability, such as a boundary between retinal pigment epithelial cells (RPE) and a Bruch membrane (BM), may be used as an index. For easiness of making an index common to a plurality of imaging view angles, a lowermost portion of the retina in the image may be used as the index. In contrast, in a case of imaging in the choroid mode, in which a DC component of an interference signal appears in a lower part of the tomographic image, an image corresponding to the interference signal is seen brighter at a lower part of the tomographic image. The optimal position for the coherence gate 64 in this case thus may be set at, for example, a position that causes the retina to be seen in the tomographic image at a part as low as possible to the extent that the retina is not turned up or a position that causes the retina to be seen upper than the part by a margin in view of the possibility that the coherence gate 64 could move from the position during imaging. The optimal position may be set on a rule basis as in the vitreous body mode described above; for example, the lowermost portion of the retina in the image may be used as the index.

In the supervised learning according to the present embodiment, an estimated distance of the coherence gate 64 that is output for a tomographic image at the optimal position is assumed to be zero to perform the learning. In creating this training data, an estimated distance of a tomographic image obtained at a position closest to the optimal position, out of obtained tomographic images, may be labeled with zero. Alternatively, for a tomographic image obtained at a position closest to the optimal position, a distance from the position to the optimal position may be estimated by shifting processing or the like, and the tomographic image may be labeled with the distance. At this time, other tomographic images may be labeled based on a time interval for a tomographic image obtained at a position closest to the optimal position and the driving speed of the driving motor 65. Alternatively, an examiner may specify an offset amount for the optimal position for the coherence gate 64 on a display screen for each imaging.

As a tomographic image used for the estimation, one resulting from imaging in a scanning direction that provides a sharp bend of the retina may be used. This reduces a risk that when the position of the coherence gate 64 is adjusted from a tomographic image obtained in a given scanning direction, the retina is seen turned up or down in tomographic images obtained in other scanning directions. In general, a bend of a retina is sharper in a horizontal direction than in a vertical direction, and thus the horizontal direction may be set as an example of the scanning direction that provides a sharp bend of the retina. However, the scanning direction set here is not limited to the horizontal direction, and any direction can be set as the scanning direction.

In the present embodiment, how long a current position of the coherence gate 64 deviates from the position of the coherence gate 64 when the tomographic image illustrated in the image (b) in FIG. 6 is obtained is measured, and this deviation is learned as an estimated distance output for a current tomographic image. Note that, in a case of the image (a) in FIG. 6, since a center portion of the retina is seen turned up, adjusting the optical path length difference precisely is difficult for the controlling unit 40 by a method of determining a position of the eye to be examined from a Z coordinate of the center portion of the retina.

The image (c) in FIG. 6 illustrates a case where the retina in the tomographic image deviates upward from the retina in the image (b) in FIG. 6 because the coherence gate 64 deviates from the optimal position. This case is unsuitable for observation and diagnosis because the peripheral portion of the retina is seen turned down. In the present embodiment, how long the position of the coherence gate 64 at this time deviates from the position of the coherence gate 64 when the tomographic image illustrated in the image (b) in FIG. 6 is obtained is measured, and this deviation is learned as an estimated distance output for the tomographic image illustrated in the image (c) in FIG. 6. In addition, in the case of the image (c) in FIG. 6, although the center portion of the retina is seen in the tomographic image at a position allowing observation, the peripheral portion is turned down, and thus adjusting the optical path length difference precisely is difficult for the controlling unit 40 by a method of determining a position of the eye to be examined from a Z coordinate of the peripheral portion of the retina.

The image (d) in FIG. 6 illustrates a tomographic image of a case where the coherence gate 64 further deviates from the optimal position in the same direction as that of the example illustrated in the image (c) in FIG. 6. This case is unsuitable for observation and diagnosis because the entire retina is seen turned up. In the present embodiment, how long the position of the coherence gate 64 at this time deviates from the position of the coherence gate 64 when the tomographic image illustrated in the image (b) in FIG. 6 is obtained is measured, and this deviation is learned as an estimated distance output for the tomographic image illustrated in the image (d) in FIG. 6. In addition, in the case of the image (d) in FIG. 6, the entire retina is seen in the tomographic image at a position allowing observation but is turned down, and thus adjusting the optical path length difference precisely is difficult for the controlling unit 40 by a method of determining a position of the eye to be examined from a Z coordinate of a representative point such as one in the center portion.

The image (e) in FIG. 6 illustrates a tomographic image of a case where the coherence gate 64 further deviates from the optimal position in the same direction as that of the example illustrated in the image (d) in FIG. 6. As a result of lowering the position of the retina in the tomographic image from the image (d) in FIG. 6, the peripheral portion of the retina is turned up, and the retina is seen in the same arrangement structure as that of the image (a) in FIG. 6. This case is unsuitable for observation and diagnosis because the center portion of the retina in the tomographic image is turned up. In the present embodiment, how long the position of the coherence gate 64 at this time deviates from the position of the coherence gate 64 when the tomographic image illustrated in the image (b) in FIG. 6 is obtained is measured, and this deviation is learned as an estimated distance output for the tomographic image illustrated in the image (e) in FIG. 6. In addition, when there are images having similar retina structures that result from generating retina signals that makes the retina seen turned up because the coherence gate 64 advances from the optimal position illustrated in the image (b) in FIG. 6 to the image (a) and the image (e) in FIG. 6 in opposite directions to each other, at least one of the images may be excluded from the training data. By not adding images having structures alike to the training data, an error in inference can be decreased.

In addition, tomographic images that are darkened resulting from being separated enough from the DC component may be excluded from the training data.

By obtaining combinations of tomographic images and estimated distances described above for many eyes to be examined, various training data items can be obtained. In addition, eyes to be examined used for the learning may include healthy eyes and affected eyes. Using the learned model obtained through learning with such various training data items, the controlling unit 40 can adjust the optical path length difference with high accuracy for eyes to be examined having different shapes.

Figure 7:
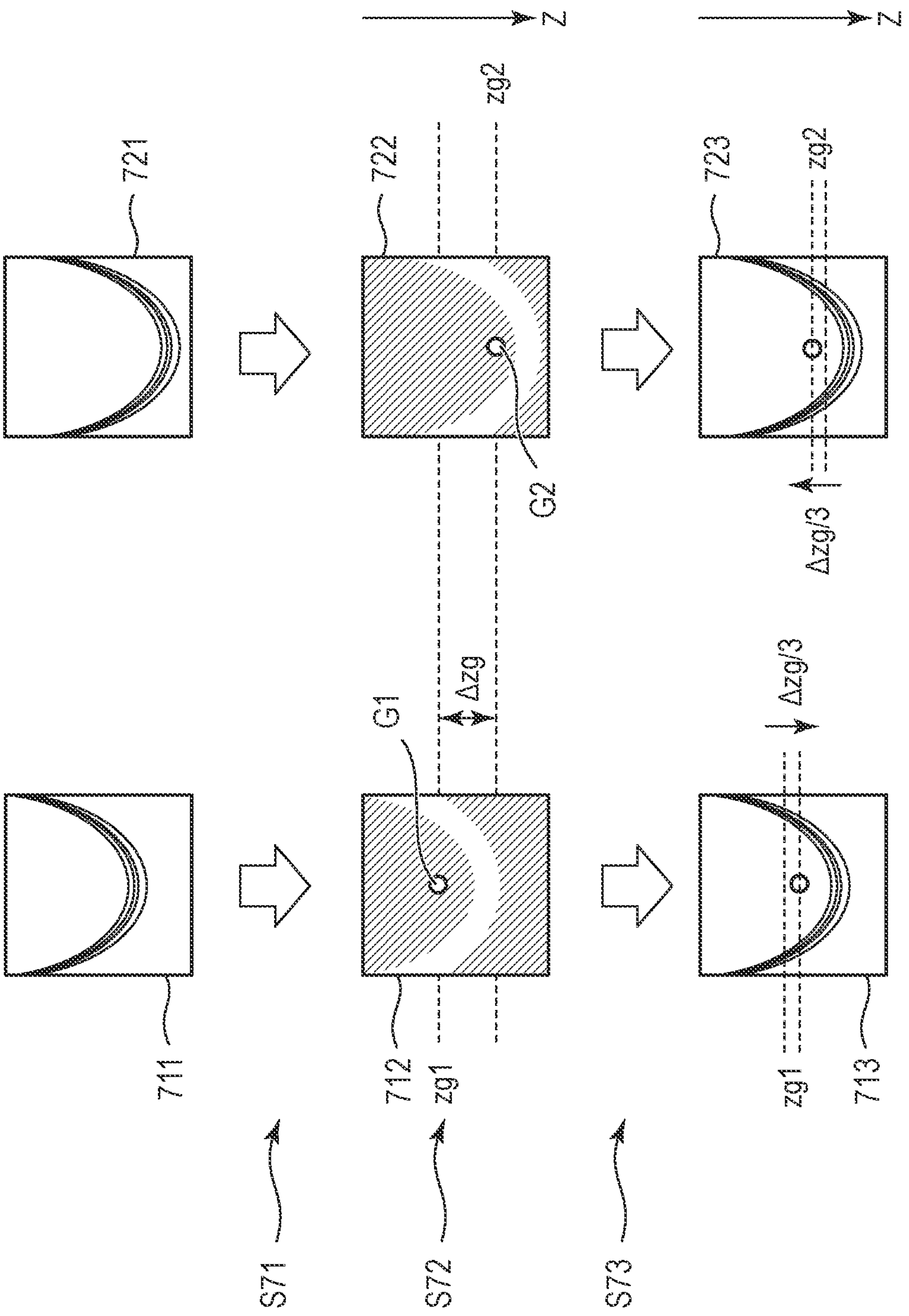
FIG. 7 illustrates an example of a course of interpolation processing on a tomographic image according to Embodiment 1.

In addition, the training data may be increased by generating interpolated images from the tomographic images obtained as the training data. An example of processing for generating an interpolated image will be described with reference to FIG. 7. FIG. 7 is a diagram describing a course of processing for interpolating a first tomographic image 711 and a second tomographic image 721 that are obtained back-to-back. An example of how the controlling unit 40 generating the training data will be described below, but note that the training data may be generated by a training unit not illustrated separate from the controlling unit 40 or may be performed by a separate apparatus.

First, in step S71, the controlling unit 40 performs binarization processing on the first tomographic image 711 and the second tomographic image 721 to generate a first binarized image 712 and a second binarized image 722, respectively. The binarization processing is performed such that an intensity value of a pixel having an intensity value equal to or higher than a preset threshold value is set at one, and an intensity value of a pixel having an intensity value lower than the threshold value is set at zero. As the threshold value, for example, a value that is 0.3 times a maximum intensity value in a tomographic image can be set. A method for the binarization processing is not limited to the above, and various methods such as an "Otsu's method" can be used. After the binarization processing, skeletonization (thinning) processing may be performed.

Next, in step S72, the controlling unit 40 calculates a Z coordinate zg1 of a gravity center G1 of the first binarized image 712 and a Z coordinate zg2 of a gravity center G2 of the second binarized image 722. The controlling unit 40 further calculates a difference Δzg between the Z coordinate zg1 and the Z coordinate zg2. Note that, in FIG. 7, a downward direction of the tomographic images is assumed to be a +Z direction. Note that any well-known method may be used as a method for calculating a Z coordinate of a gravity center of a binarized image.

Next, in step S73, the controlling unit 40 shifts the first tomographic image 711 in the Z direction by +Δzg/3 to generate a first interpolated image 713. Likewise, the controlling unit 40 shifts the second tomographic image 721 in the Z direction by −Δzg/3 to generate a second interpolated image 723.

Here, estimated distances as ground truth labels (ground truth) for the first tomographic image 711 and the second tomographic image 721 are defined as estimated distances cz711 and cz721. At this time, an estimated distance cz713 corresponding to the first interpolated image 713 and an estimated distance cz723 corresponding to the second interpolated image 723 may be determined by performing interpolation from the estimated distances cz711 and cz721 as shown by the following Formula (1) and Formula (2).

$$cz713=cz711+(cz721-cz711)/3 \quad \text{Formula (1)}$$

$$cz723=cz721-(cz721-cz711)/3 \quad \text{Formula (2)}$$

In this manner, the controlling unit 40 generates two new interpolated images from the first tomographic image 711 and the second tomographic image 721, by which the training data can be increased. By generating the interpolated images and performing the learning, intervals between ground truth labels of estimated distances can be shortened, and inference resolution can be improved.

Although an example in which one interpolated image is generated from each of the first tomographic image 711 and the second tomographic image 721 is described, two or more interpolated images may be generated from each tomographic image. For example, in a case where two interpolated images are to be generated from each of the first tomographic image 711 and the second tomographic image 721, four interpolated images are generated in total by shifting the first tomographic image 711 in the Z direction by $+\Delta zg/5$ to generate an interpolated image, shifting the first tomographic image 711 in the Z direction by $+2\Delta zg/5$ to generate an interpolated image, shifting the second tomographic image 721 in the Z direction by $-\Delta zg/5$ to generate an interpolated image, and shifting the second tomographic image 721 in the Z direction by $-2\times\Delta zg/5$ to generate an interpolated image. Estimated distances as ground truth labels for these interpolated images may be determined by performing interpolation from the estimated distances as ground truth labels corresponding to the first tomographic image 711 and the second tomographic image 721, as described above.

Alternatively, the training data may be increased by generating new images with a generative adversarial network (GAN).

In addition, the training data may be increased by a plurality of images by performing shifting processing on one tomographic image in a perpendicular direction (a depth direction of the retina). An example of how to perform the shifting processing will be described with reference to FIG. 8. An image (a) in FIG. 8 illustrates an example of a tomographic image serving as an original for the shifting processing (original image).

Figure 8:
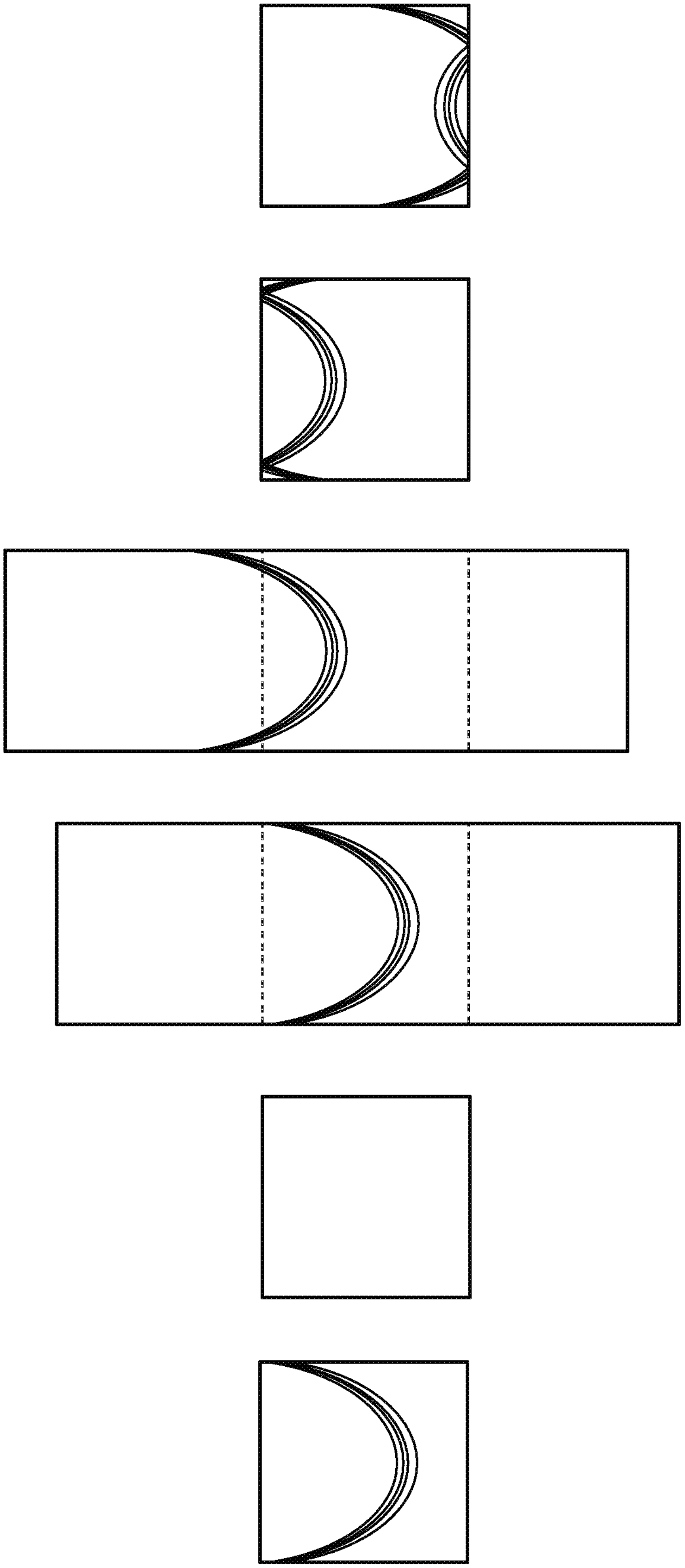
FIG. 8 illustrates an example of a course of shifting processing on a tomographic image according to Embodiment 1.

An image (b) in FIG. 8 illustrates an example of a background image. The background image has the same size in pixels as that of the original image and is generated from pixels each having an intensity value that is an intensity value of a background of the original image (pixels not in the retina). The intensity value of the pixels may be set at an average intensity value of the original image or an intensity value that is determined to be of the background based on a frequency distribution of intensity values of the original image. For example, the intensity value may be set at an intensity value that is randomly selected from intensity values of pixels accounting for 70% of the entire frequency distribution from the darkest. The intensity value of the background image may be zero. A method for generating the background image is not limited to the above, and the background image can be generated by any appropriate method.

Next, generated background images are joined to the original image from above and below the original image to generate a joined image (an image (c) in FIG. 8). Then, the joined image is shifted by a predetermined shifting amount (an image (d) in FIG. 8).

Next, portions of the retina that protrude from a region of the original image (inside region between upper and lower dotted lines in the image (d) in FIG. 8) may be displayed such that the portions are turned down at a boundary of the protrusion (a position of one of the up and down dotted lines in the image (d) in FIG. 8) (an image (e) in FIG. 8). At this time, the portions of the retina may be detected based on magnitudes of intensity values. For example, when intensity values of pixels protruding from the boundary are 1.5 times or greater intensity values of pixels at a position symmetric about the boundary, the pixels protruding from the boundary may be regarded as those of the retina. Alternatively, the portions of the retina may be detected in such a manner that whether the pixels protruding from the boundary are sufficient large with respect to an average value or a median of the intensity values of the background image. A method for detecting the portions of the retina is not limited to the above, and the portions can be detected by any method.

In addition, with consideration given to the fact that a strength of a signal attenuates as the signal is separated from a DC component due to decrease in coherence, processing for attenuating intensity values based on a distance of the signal from the DC component or the shifting amount may be performed in the shifting processing. For example, in a case where an upper part of the tomographic image illustrated in the image (a) in FIG. 8 corresponding to the DC component, and in a case where the tomographic image is shifted upward and turned down as illustrated in the image (d) in FIG. 8, an attenuation factor of a signal of a turned portion may be set to be small or zero. Conversely, in a case where the tomographic image is shifted downward and turned up in an opposite manner to that of the image (d) in FIG. 8, the attenuation factor of the signal of a turned portion may be set to be large (an image (f) in FIG. 8). Alternatively, with consideration given to the fact that intensity values level off when a signal intensity is high, the attenuation factor may be set based on magnitudes of original intensity values, such as setting the attenuation factor lower or setting no attenuation factor when the intensity values level off.

By performing the shifting processing with a plurality of shifting amounts being set, a plurality of shifted images is generated, and the training data can be increased. A relation between a driving amount of the coherence gate 64 and a shifting amount of the retina in the tomographic image is set based on optical specifications of the apparatus, a method for signal processing (method for setting the number of data items), and the like. As an example, in a case where a depth range of imaging tomographic images is 5 mm in terms of a distance in the air, and the number of pixels of a tomographic image in a longitudinal direction is 100 pixels, the shifting amount is equivalent to a driving amount of 50 μm per pixel. A required adjustment resolution for the coherence gate 64 may be set by setting the required adjustment resolution from the number of pixels of the tomographic image in the longitudinal direction and converting the number of pixels into the driving amount of the coherence gate 64. Furthermore, the shifting amount may be set based on the required adjustment resolution of the coherence gate 64, with which a plurality of tomographic images may be generated in a pseudo manner. At this time, the learned model may be obtained from training data that in which input data is new tomographic images obtained by shifting a tomographic image of an eye to be examined in a depth direction of the eye to be examined by a predetermined shifting amount and that includes the shifting amounts as ground truth. Note that such training data can be used not only for the coherence gate 64 as an example of the optical path length difference changing unit, but also, for example, in a case where a driving amount of the optical head, the focus lens 58, or the like is used as the shifting amount. That is, the controlling unit 40 may use such learned model to determine a driving amount of the driving unit for driving an optical member included in the optical coherence tomography apparatus (coherence gate 64, optical head, focus lens 58, etc.) from obtained tomographic images.

In addition, trimming processing may be performed on an image of a wide angle of view to generate an image of a narrow angle of view in a pseudo manner, and the image of a narrow angle of view may be added to the training data. In the trimming processing, a center of the image may be cut out, or a portion away from the center may be cut out. In addition, a tomographic image of a retina in myopia or high myopia may be generated in a pseudo manner from one tomographic image and added to the training data.

Figure 9:
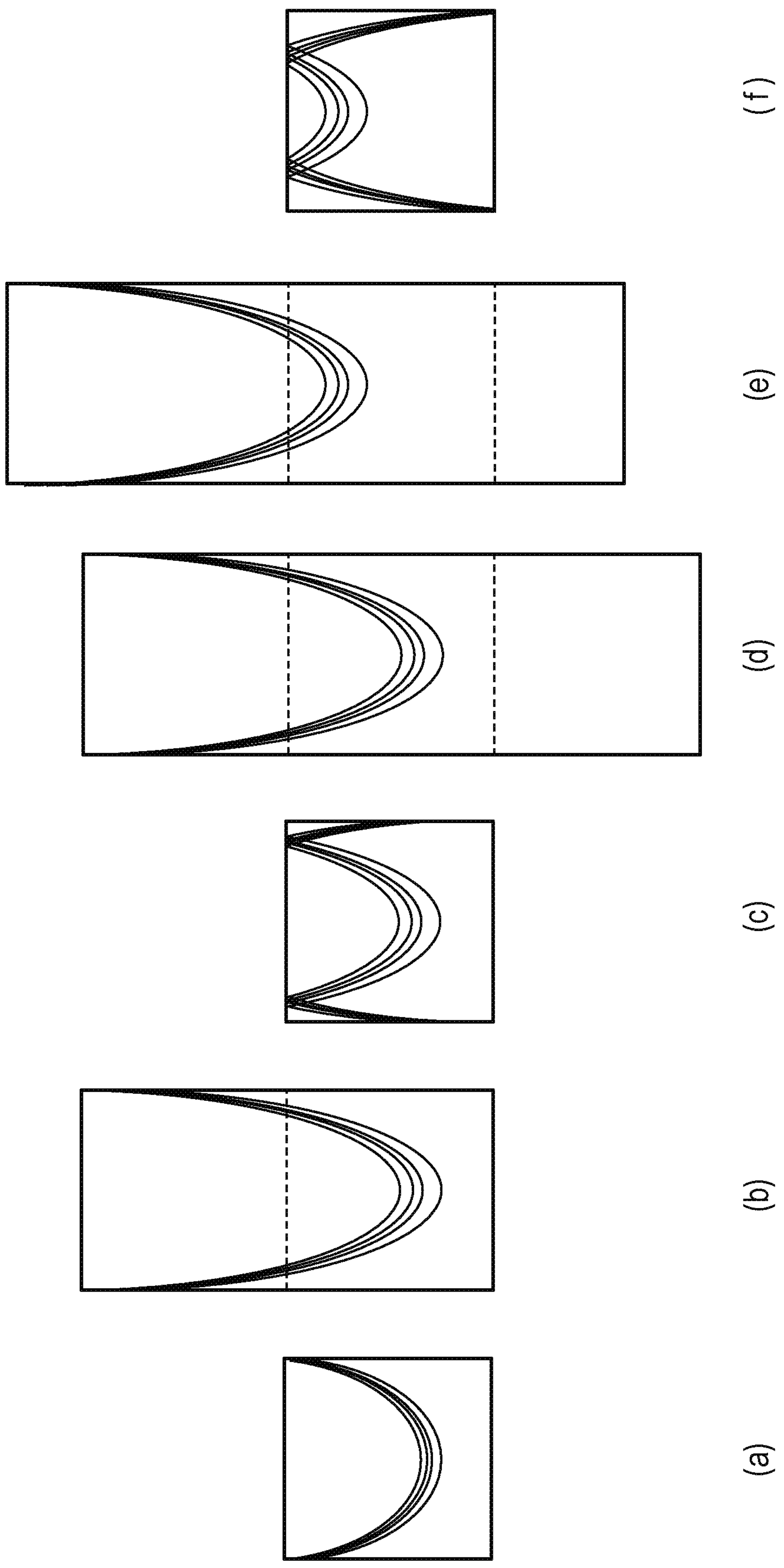
FIG. 9 illustrates an example of a method for generating a pseudo myopia image according to Embodiment 1.

A method for generating a pseudo myopia image will be described with reference to FIG. 9. An image (a) in FIG. 9 illustrates an example of a tomographic image serving as an original for a pseudo myopia image (original image). First, the original image is enlarged in a longitudinal direction, by which an enlarged image is generated (an image (b) in FIG. 9). As an example of a method for generating the enlarged image, pixels on each column (A-scan) of the tomographic image can be moved upward. An amount of the upward movement may be determined based on, for example, a quadratic function of a lateral distance from a center of the tomographic image to the column. A sharpness of a bend of a shape of the retina can be adjusted with coefficients of the quadratic function, and images of a plurality of bend shapes may be created and used in the training data. In a case where an enlarged image is generated by moving pixels, pixels that become vacant due to the movement may be embedded with pixels having an average intensity value of neighbor pixels or with pixels having a representative intensity value of a background region. Here, the background region may be determined based on, for example, a frequency distribution and may be randomly selected from pixels accounting for 70% of the entire frequency distribution from the darkest.

Next, by the same method as that for the image (e) in FIG. 8, portions protruding from a region of the original image (portion above a dotted line illustrated in the image (b) in FIG. 9) may be displayed such that the portion is turned down at a boundary of the protrusion (dotted line in the image (b) in FIG. 9) (an image (c) in FIG. 9). In this manner, a pseudo myopia image as illustrated in the image (c) in FIG. 9 can be generated.

In addition, training data on pseudo myopia images may be increased by shifting processing. An example of the shifting processing will be described below. First, the same background image as that illustrated in the image (b) in FIG. 8 is generated. The background image is joined to the enlarged image illustrated in the image (b) in FIG. 9, by which a joined image is generated (an image (d) in FIG. 9). Next, the joined image is shifted by a predetermined shifting amount (an image (e) in FIG. 9). Subsequently, by the same method as that for the image (e) in FIG. 8, portions protruding from a region of the original image (portion above a dotted line illustrated in the image (e) in FIG. 9) may be displayed such that the portion is turned down at a boundary of the protrusion (upper dotted line in the image (e) in FIG. 9) (an image (f) in FIG. 9). In this manner, an image resulting from shifting a pseudo myopia image, as illustrated in the image (f) in FIG. 9 can be generated. By setting a plurality of shifting amounts, training data on pseudo myopia images may be increased.

Similarly to the method for generating pseudo myopia images, tomographic images of retinae having a dome shape and retinae having various shapes may be generated in a pseudo manner by moving pixels on each column (A-scan) of a tomographic image and added to the training data. In addition, these pseudo images may be generated by referring to segmentation information on a tomographic image of a retina serving as an original and modifying the segmentation information. In addition, tomographic images of retinal detachment may be generated in a pseudo manner by referring to the segmentation information.

Although a case where the training data is data on an eye to be examined has been described, the training data can be generated also by using a model of an eye. In this case, a large number of training data items can be generated more efficiently.

The learning according to the present embodiment can be performed with the training data as described above by a backpropagation method, which adjusts a weight coefficient of each edge connecting nodes so as to establish a relationship between an input layer and an output layer of each neural network. Specifically, first, for an input data input into an input layer of a machine learning model, output data output from an output layer of a neural network and errors between the output data and the training data are obtained. Note that errors between the output data from the neural network and supervisory data may be calculated with a loss function. Next, based on the obtained errors, connection weight coefficients and the like between nodes of the neural network are updated by the backpropagation method so as to reduce the errors. The backpropagation method is a method for adjusting the connection weight coefficients and the like between the nodes of each neural network so as to reduce the errors. Note that, in addition to the backpropagation method described above, a wide variety of well-known learning methods including what one calls stacked autoencoder, dropout, noise addition, batch normalization, and sparsity regularization, and the like may be used in combination to improve processing accuracy.

When data is input into a learned model that has trained with such training data, data conforming to a design of the learned model is output. For example, data probably corresponds to input data is output according to tendency that is trained with the training data. In the present embodiment, when a tomographic image is input into a learned model that has trained with the training data described above, an estimated distance to the optimal position of the coherence gate 64 is output.

Based on the estimated distance, the controlling unit 40 determines a driving amount of the driving motor 65 to drive the coherence gate 64 next. The controlling unit 40 thus can function as an example of a determining unit that determines, using the learned model, a driving amount of the driving unit driving the optical path length difference changing unit from a tomographic image of an eye to be examined. Note that the driving amount determined by the determining unit corresponds to an actual driving amount of the driving unit and not necessarily the same as an output from the learned model. The determining unit may use the output from the learned model to determine the driving amount of the driving unit; for example, a value resulting from converting the estimated distance output from the learned model into a number of revolutions or a number of steps of the driving unit may be used as the driving amount. Alternatively, the determining unit may determine the driving amount of the driving unit based on a value resulting from adding a predetermined offset value or the like to the estimated distance.

In a case where the learned model is a regression model, the controlling unit 40 can set an estimated distance output from the learned model as a driving amount of the driving motor 65 to drive the coherence gate 64 next. In contrast, in a case where the learned model is a classification model, data output from the learned model may be a single or a plurality of estimated distance classes and a probability for the class. In this case, the controlling unit 40 may be configured so as to interpret an output result from the learned model as a probability for each estimated distance class by using a softmax function in a final layer of the machine learning model.

In addition, the controlling unit 40 may adjust the estimated distance output in step S43 according to the probability output from the learned model. As an example, in a case where probabilities for two output classes are comparable to each other, a distance equivalent to a center distance of the classes may be determined to be an estimated distance to be output. Note that a method for determining the estimated distance output in step S43 from estimated distances of a plurality of classes output from the learned model is not limited to the above. For example, the controlling unit 40 may cause the display unit 70 to display the estimated distances of the plurality of classes output from the learned model and the probabilities for the estimated distances, and an examiner may select an estimated distance or the driving amount of the driving motor 65 to be output in step S43 according to the display. In this case, the controlling unit 40 can determine the estimated distance or the driving amount to be output according to instructions from an operator.

In a learning method for reinforcement learning, the controlling unit 40 obtains tomographic images while shifting the coherence gate 64 in random directions by random amounts and evaluates the tomographic images. As an evaluation index, for example, a brightness of an image can be used.

In a case of imaging in the vitreous body mode, in which a DC component of an interference signal appears in an upper part of the tomographic image, an image corresponding to the interference signal is seen brighter at an upper part of the tomographic image due to characteristics of coherence. Therefore, using a brightness of an image as an evaluation index, adjustment processing can be performed so that a retina can be seen in a tomographic image. The evaluation index for tomographic images used here is not limited to the above, and an appropriate evaluation index can be set according to an adjustment criterion.

After evaluating the tomographic images, the controlling unit 40 moves the coherence gate 64 at random again to obtain tomographic images and evaluates the newly obtained tomographic images. The controlling unit 40 then calculates differences between evaluation values and uses the differences as rewards to train the neural network by the backpropagation method so that a maximum reward is obtained. A target for the reinforcement learning may be set at, for example, reaching a position that maximizes the reward in a shortest time.

A case where the tomographic image illustrated in the image (b) in FIG. 6 is obtained before the coherence gate 64 is moved will be described as an example. In an example of the reinforcement learning, the controlling unit 40 first obtains an evaluation value Eb of the tomographic image at this position. Next, assume that a tomographic image as illustrated in the image (c) in FIG. 6 is obtained as a result of obtaining a tomographic image by moving the coherence gate 64 at random. The controlling unit 40 obtains an evaluation value Ec of the tomographic image at this position. Using a difference Ec−Eb between the evaluation values as a reward, the controlling unit 40 performs the reinforcement learning of the machine learning model.

By repeating such a learning operation, the machine learning model can learn tomographic images and feature quantities for outputting estimated distances to optimal positions of the coherence gate 64 corresponding to the tomographic images. For such reinforcement learning, well-known what one calls a Q-learning algorithm may be used, which will not described in detail here. Note that, as an algorithm of the reinforcement learning, for example, Saras, the Monte Carlo method, or a bandit algorithm may be used.

Also in the reinforcement learning, the learning may be performed by using a model of an eye. Furthermore, in the reinforcement learning, the learned model obtained in advance through learning with the model of an eye may be subjected to transfer learning in which additional learning is performed by using a human eye.

Note that the machine learning algorithm for the learned model is not limited to the deep learning using the illustrated neural network. The machine learning algorithm used for the processing may be another machine learning algorithm using, for example, a support vector machine or a Bayesian network.

In a case where the coherence gate 64 is driven based on the estimated distance obtained by using the learned model as described above, the driving amount may be offset in a direction in which a tomographic image is shifted downward from a tomographic image obtained at the estimated distance. An offset amount can be set at, for example, ⅕ of a range in the Z direction of the imaging for the tomographic image. In this manner, the entire retina can be easily made to be seen in the tomographic image without being turned down.

The above description is given of an example of using a learned model in which input data is tomographic images that are images obtained by using combined light of the measurement light and the reference light. However, the tomographic images input into the learned model are not limited to the above and may be tomographic images generated by performing any image processing and the like on images obtained by using the combined light. For example, tomographic images obtained by performing correction processing on images obtained by using the combined light may be used as the input data of the learned model. The correction processing can be performed by the controlling unit 40, and the controlling unit 40 can function as an example of a correcting unit that performs the correction processing on an image. In this case, tomographic images subjected to image processing such as the correction processing can be similarly used as input data of the training data.

An example of the correction processing may be processing for binarizing a tomographic image. The binarization processing is performed such that an intensity value of a pixel having an intensity value equal to or higher than a preset threshold value is set at one, and an intensity value of a pixel having an intensity value lower than the threshold value is set at zero. As the threshold value, for example, a value that is 0.3 times a maximum intensity value can be set. A method for the binarization processing is not limited to the above, and various methods such as the "Otsu's method" can be used. After the binarization processing, skeletonization processing may be performed.

An example of the correction processing may be processing for enlarging or reducing a tomographic image in a longitudinal direction based on data on an eye axial length or a visual acuity that is separately input into the controlling unit 40. In a case of reducing a tomographic image in the longitudinal direction, for example, reduction processing can be performed while a Z coordinate of an uppermost pixel out of pixels having intensity values equal to or higher than a threshold value in the tomographic image is fixed. In an edge portion, a region of pixels that are made to have no intensity value by the reduction may be embedded with pixels having an average intensity value of neighbor pixels.

Furthermore, an example of the correction processing may be processing for extracting part of a tomographic image. An example of processing for extracting part of a tomographic image will be described with reference to FIG. 10. An image (a) in FIG. 10 illustrates an example of a tomographic image before the extraction. In the image (a) in FIG. 10, an inside between two dotted lines indicates a center portion of the tomographic image, and portions outside the two dotted lines indicate peripheral portions of the tomographic image.

The processing for extracting part of the tomographic image may be, for example, processing for extracting only the center portion as illustrated in an image (b) in FIG. 10. Alternatively, the processing for extracting part of the tomographic image may be processing for extracting only the peripheral portions as illustrated in an image (c) in FIG. 10. Alternatively, the processing for extracting part of the tomographic image may be processing for extracting only some representative columns (A-scan data items) as illustrated in an image (d) in FIG. 10. Alternatively, an examiner may select a region to be extracted from the tomographic image while watching the display unit 70. By extracting a partial region in this manner, features of more interest can be extracted, and a computational load can be reduced at the same time.

Figure 11:
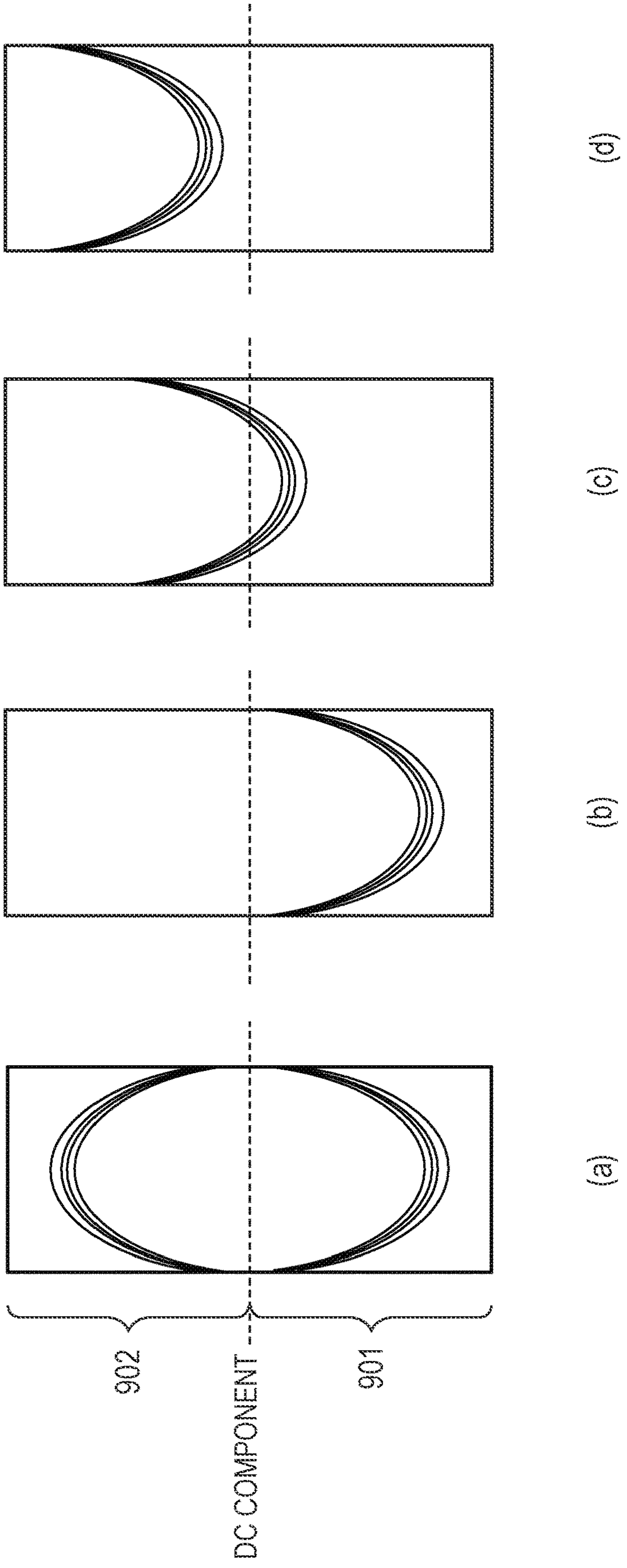
FIG. 11 illustrates an example of processing using a mirror-image part according to Embodiment 1.

Furthermore, an example of the correction processing may be processing using a mirror-image part. This processing will be described with reference to FIG. 11. An image (a) in FIG. 11 illustrates an example of a signal corresponding to a tomographic image that is obtained by performing Fourier transform on an interference signal obtained by the OCT apparatus. Of the signal illustrated in the image (a) in FIG. 11, a mirror-image part 902 mentioned here is a portion opposite side of a DC component to a real-image part 901 that is displayed on the display unit 70 as a tomographic image.

In an example of the processing using a mirror-image part, an image including both the real-image part 901 and the mirror-image part 902 is used as input data of the learned model. Note that an example of the processing using a mirror-image part is not limited to the above.

For example, in another example of the processing using a mirror-image part, as illustrated in an image (b) in FIG. 11, an image in which only image components forming a downward convex to be observed are extracted by removing image components forming an upward convex from the tomographic image is generated. Processing for generating the image in which only the image components forming the downward convex are extracted is an example of processing for generating an image in which some image components are extracted from the tomographic image including both the real-image part 901 and the mirror-image part 902. This processing may be performed using a machine learning model that generates an image in which only the image components forming the downward convex are seen, from an image in which the image components forming the upward convex and the image components forming the downward convex are seen. Alternatively, the image in which only the image components forming the downward convex are seen may be generated by using segmentation processing to extract the image components forming the upward convex and the image components forming the downward convex and to leave only the image components forming the downward convex. Alternatively, an image in which only image components forming a downward convex are seen may be generated by using other type of processing such as rule-based one.

In a case where the coherence gate 64 deviates from the optimal position, at least some of components forming a downward convex may be seen in the mirror-image part 902, as illustrated in an image (c) and an image (d) in FIG. 11. Therefore, the estimated distance of the coherence gate 64 may be obtained from a learned model using an input image being an image that includes both regions of the real-image part 901 and the mirror-image part 902 and in which only image components forming a downward convex is extracted. In this case, the image components forming the downward convex seen in the mirror-image part 902 can be used for the learning or inference, by which accuracy of the inference can be improved.

Although an example of a case where the DC component of the real-image part 901 is on a vitreous body side, this is not limitative. In a case where the DC component of the real-image part 901 is on a choroid side, a position at which the mirror image is turned down with respect to the real image is below the real image, but the same idea can be applied to this case.

Furthermore, an example of the correction processing may include at least one of smoothing processing and contrast adjustment processing. This enables improvement in quality of tomographic images and enables improvement in accuracy of inference processing.

As a learned model used for determining an estimated distance of the coherence gate 64, the controlling unit 40 may include a plurality of learned models that corresponds to a plurality of imaging conditions and conditions of eyes to be examined. In this case, the controlling unit 40 selects a model to be used for the inference according to an imaging condition and a condition of an eye to be examined. The controlling unit 40 thus can function as an example of a selecting unit that selects a learned model corresponding to obtained tomographic images. In this case, the controlling unit 40 functioning as a determining unit can determine the driving amount of the driving unit from an obtained tomographic image using the selected learned model. The controlling unit 40 can include learned models for each imaging view angle or depth range of imaging, which is an example of the imaging condition, for example.

In addition, in a case where a single program is used to perform image processing for a plurality of models of OCT apparatuses, the controlling unit 40 can include learned models that corresponds to the models of the OCT apparatuses. This enables, for example, a single program to be applied to both an SD-OCT apparatus and an SS-OCT apparatus.

The imaging conditions may include imaging modes such as a mode for obtaining a reverse image, which is suitable for observing a deep portion such as a choroid (choroid mode, or an enhanced depth imaging: EDI) and a mode for obtaining a normal image (vitreous body mode). In this case, the controlling unit 40 can include, for example, learned models that corresponds to both the mode for obtaining a reverse image and the mode for obtaining a normal image. There is a difference between the vitreous body mode and the choroid mode in that the vitreous body mode causes a retina to be seen in an upper part of a tomographic image brighter, while the choroid mode causes a retina to be seen in a lower part of a tomographic image darker, and thus a change in how a retina is seen when the coherence gate 64 is driven differs between the vitreous body mode and the choroid mode. For example, when the coherence gate 64 is driven from a position of the image (b) in FIG. 6 in a direction that causes the retina to move upward, the retina becomes brighter in an image in the vitreous body mode, while the retina becomes darker in an image in the choroid mode. In the vitreous body mode, when the coherence gate 64 is driven from the position of the image (b) in FIG. 6 in a direction that causes the tomographic image to move upward, an image in which the retina is seen bright as the image (d) in FIG. 6 is obtained. In contrast, in the choroid mode, when the coherence gate 64 is driven from the position of the image (b) in FIG. 6 in a direction that causes the tomographic image to move downward, an image in which the retina is seen bright as the image (d) in FIG. 6 is obtained. Since behavior that appears when the coherence gate 64 is driven thus differs between the vitreous body mode and the choroid mode, these modes can be supported by separately preparing learned models that correspond to the respective modes. At this time, as the learned model, any one of a plurality of learned models that corresponds to a plurality of target positions for the optical path length difference changing unit may be selected, the plurality of target positions each being a target for the adjustment of the optical path length difference.

In addition, the imaging conditions may include a mode for generating a panoramic image. In this case, the controlling unit 40 can include, as a learned model that corresponds to the mode for generating a panoramic image, a learned model that is obtained through learning with tomographic images for which a position of fixation is changed by the internal fixation lamp 110.

Examples of a condition of an eye to be examined include whether the eye to be examined is myopia or high myopia or not. For example, the controlling unit 40 may include a learned model that has trained with eyes to be examined being myopia and a learned model that has trained with eyes to be examined not being myopia, and which of the learned models is to be applied may be selected by the controlling unit 40 or an examiner who has referred to patient data.

The controlling unit 40 may perform processing for converting an estimated distance obtained by using a learned model into a driving amount of the driving motor 65 based on an imaging condition, a condition of an eye to be examined, an offset amount, or the like. For example, the controlling unit 40 may correct an obtained estimated distance and convert the estimated distance into the driving amount of the driving motor 65 according to an imaging condition (the imaging view angle, the depth range of imaging, the model, whether the mode is the vitreous body mode or the choroid mode) or a condition of an eye to be examined (whether the eye is myopia or not). The controlling unit 40 may convert a value obtained by offsetting an obtained estimated distance into the driving amount of the driving motor 65 based on an optimal position for a retina in a tomographic image that has been set by an examiner. By configuring the controlling unit 40 to perform the converting processing as described above, the number and a capacity of learned models included in the controlling unit 40 can be reduced as compared with a case where the controlling unit 40 includes a plurality of learned models corresponding to the imaging conditions. Furthermore, this configuration reduces trouble of reloading a learned model whenever an imaging condition is changed.

Figure 12:
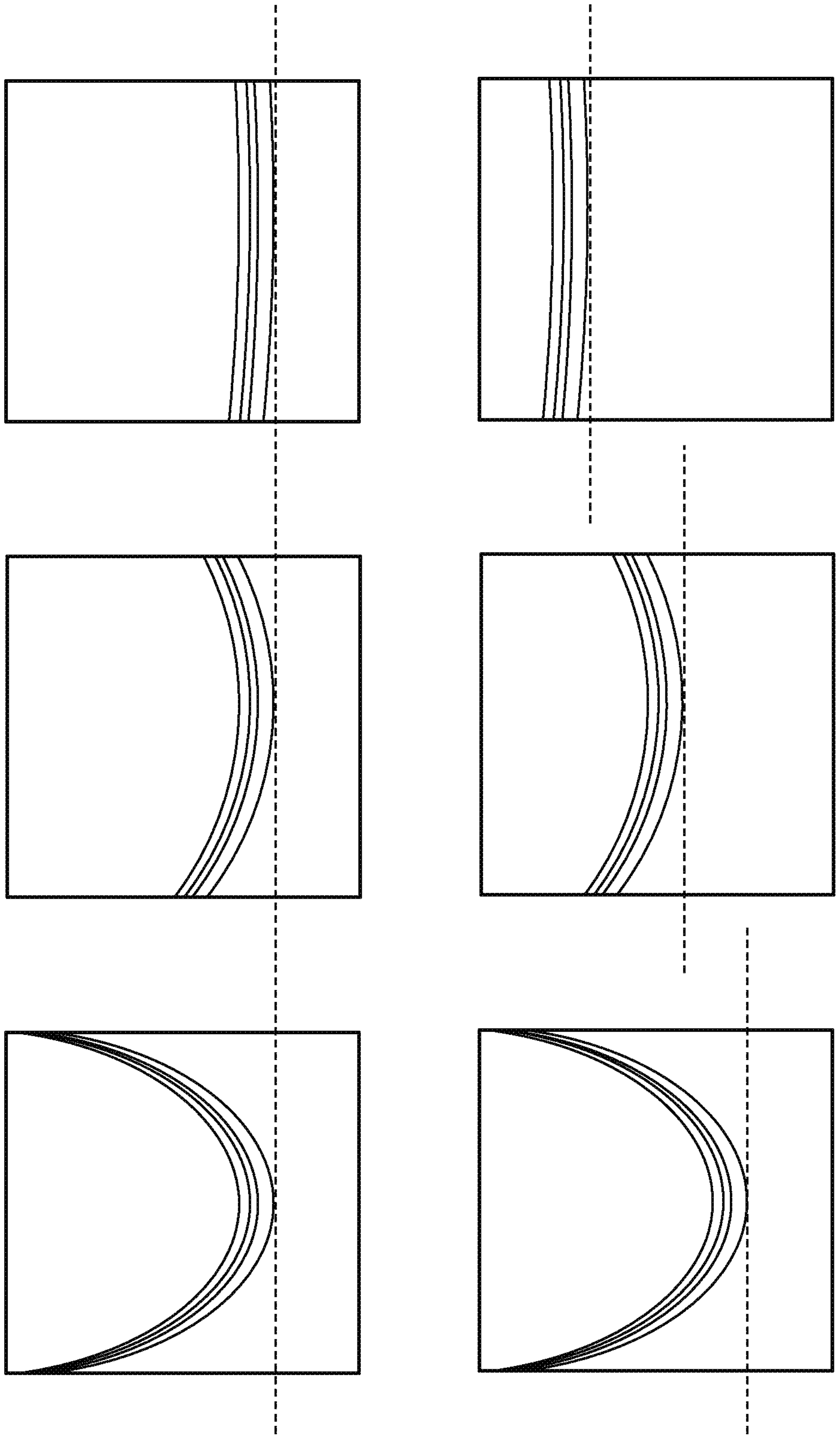
FIG. 12 illustrates an example of offsetting processing according to Embodiment 1.

To this end, for example, as illustrated in an image (a) in FIG. 12, a correct position of the coherence gate 64 may be determined to be a position of the coherence gate 64 when a lowermost part of a retina in a tomographic image is located at a standard height, and a common learning model may be generated for different imaging view angles. After an estimated distance is obtained with this learned model, offsetting processing may be performed such that the lowermost part of the retina becomes located at an upper position with a narrower angle of view as illustrated in an image (b) in FIG. 12. The offset amount here can be determined as appropriate on a rule basis based on an imaging view angle. The offsetting processing here may be processing for driving the coherence gate 64 by a distance resulting from subtracting the offset amount from the estimated distance or may be processing for driving the coherence gate 64 by the estimated distance and then driving the coherence gate 64 again by the offset amount. This offsetting processing may be performed only when a condition for step S46 described later is satisfied. A method for setting a criterion for generating the common learning model is not limited to the above, and various methods can be used. That is, the controlling unit 40 as an example of the determining unit may determine a driving amount of the driving motor 65 as an example of the driving unit by adding an offset amount corresponding to an imaging view angle included in an imaging condition to an output value to be described later (or a small value to be described later). For example, the offset amount corresponding to a narrow imaging view angle may be set such that a retina region in a tomographic image obtained by imaging with the narrow imaging view angle is shifted closer to a vitreous body region than a retina region in a tomographic image obtained by imaging with a wide imaging view angle. At this time, the offset amount corresponding to the wide imaging view angle may be zero. Alternatively, the offset amount corresponding to a wide imaging view angle may be set such that a retina region in a tomographic image obtained by imaging with the wide imaging view angle is shifted away from the vitreous body region than a retina region in a tomographic image obtained by imaging with a narrow imaging view angle. At this time, the offset amount corresponding to the narrow imaging view angle may be zero.

In addition, the controlling unit 40 may be configured to perform trimming processing for leaving a center portion in a case of a large imaging view angle or depth range of imaging and not to perform the trimming processing in a case of a small imaging view angle or depth range of imaging. In this case, view angles or a depth ranges of tomographic images input into a learned model can be standardized. At this time, the controlling unit 40 may adjust an image size by thinning or interpolating an image as necessary. Performing such processing enables a common learned model to be used for different imaging view angles or depth ranges of imaging. Therefore, the number and a capacity of learned models included in the controlling unit 40 can be reduced as compared with a case where the controlling unit 40 includes a plurality of learned models corresponding to the imaging conditions.

Evaluation of a performance of a created learned model may be conducted based on a difference between an estimated distance and a ground truth label. In addition, the shifting processing described with reference to FIG. 8 may be used to move the coherence gate 64 by an estimated distance to generate a pseudo adjusted image, and the pseudo adjusted image may be evaluated qualitatively or on a rule basis.

In the above-described manner, in step S43, the controlling unit 40 uses a learned model to obtain an estimated distance of the coherence gate 64 from a tomographic image. As the controlling unit 40 obtains the estimated distance, the processing proceeds to step S44.

In step S44, the controlling unit 40 increments the number i of trials by one. As the controlling unit 40 increments the number i of trials, the processing proceeds to step S45.

In step S45, the controlling unit 40 determines whether the estimated distance obtained in step S43 is equal to or lower than the target distance. The target distance is an index of a distance for achieving a target adjustment accuracy and can be expressed by, for example, a deviation amount (distance) from an adjusted position as a target. The target distance may be set at, for example, 300 μm. Alternatively, the target distance may be determined based on an imaging range of a retina and the number of pixels of a tomographic image. In addition, the target distance may be set for each examiner and every imaging. The controlling unit 40 may have an imaging mode for each of a plurality of target distances, and the target distance may be set according to an imaging mode selected by an examiner. In a case where the estimated distance is determined to be equal to or lower than the target distance, the processing proceeds to step S46.

In step S46, the controlling unit 40 determines whether the estimated distance obtained in step S43 is equal to or lower than the target distance for a predetermined consecutive number of times N. The predetermined consecutive number of times N here is an index that indicates a stability for determining whether to finish the fine adjustment. The predetermined consecutive number of times N can be set at, for example, three. In a case where the estimated distance is determined to be "equal to or lower than the target distance for the predetermined consecutive number of times N", the controlling unit 40 finishes the fine adjustment processing of coherence gate. The predetermined consecutive number of times N can be set at one, and when the condition is satisfied in step S46, the adjustment can be finished by the determination performed only once. Note that the predetermined consecutive number of times N is not limited to three and one and may be set at any number according to a desired configuration.

In contrast, in a case where the estimated distance is determined not to be "equal to or lower than the target distance for the predetermined consecutive number of times", the processing proceeds to step S47. In step S47, the controlling unit 40 drives the coherence gate 64 by the estimated distance. The processing then returns to step S42, where the controlling unit 40 performs the processing according to the flow as described above again.

In step S46, whether the estimated distance obtained in step S43 is equal to or lower than the target distance for a certain number of times out of the predetermined consecutive number of times may be used as an index for the determination. For example, whether the estimated distance is equal to or lower than the target distance for three times or greater out of five consecutive times may be used as an index for the determination. Note that the predetermined consecutive number of times and the certain number of times are not limited to the above and may be set at any number according to a desired configuration.

In a case where the estimated distance is determined not to be equal to or lower than the target distance in step S45, the processing proceeds to step S48. In step S48, the controlling unit 40 determines whether the number i of trials is lower than a preset maximum number of trial. The maximum number of trial can be set at, for example, five. Note that the maximum number of trial may be set at any number according to a desired configuration.

In a case where the number i of trials is determined to be lower than the maximum number of trial in step S48, the processing proceeds to step S49. In step S49, the controlling unit 40 drives the coherence gate 64 by the estimated distance. In a case where the estimated distance is greater than a predetermined distance threshold value Lmax, the driving amount of the driving in step S49 may be the distance threshold value Lmax. The distance threshold value Lmax can be set at, for example, the same value as that of a depth range of a tomographic image. Alternatively, the distance threshold value Lmax may be set at a small value such as ⅕ of the depth range of a tomographic image for little-by-little driving. However, the distance threshold value Lmax may be set at any value according to a desired configuration. That is, the controlling unit 40 as an example of the determination unit may determine whether a value output from the learned model receiving the obtained tomographic image is greater than the threshold value. At this time, in a case where the output value is equal to or lower than the threshold value, the controlling unit 40 as an example of the determining unit may determine the output value as the driving amount. In addition, in a case where the output value is greater than the threshold value, the controlling unit 40 may determine the threshold value as the driving amount. Alternatively, the controlling unit 40 as an example of the determination unit may determine whether the driving amount of the driving motor 65 as an example of the driving unit is greater than a threshold value. At this time, in a case where the driving amount is greater than the threshold value, the controlling unit 40 as an example of the determining unit may determine the threshold value as the driving amount.

The distance by which the controlling unit 40 drives the coherence gate 64 in step S49 may be set according to the estimated distance. For example, the distance by which the coherence gate 64 is to be driven can be set at half the estimated distance. This increases the number of the inference, so that converging adjustment can be performed more robustly. In this case, the maximum number of trial in step S48 can be set to be greater than 5 in the above-described case, for example, set at 15. Note that the maximum number of trial may be set at any number according to a desired configuration. The distance by which the coherence gate 64 in this case is not limited to the half the estimated distance and can be set optionally according to the estimated distance. That is, the controlling unit 40 as an example of the determining unit may determine the driving amount of the driving motor 65 as an example of the driving unit by converting the value output from the learned model receiving the obtained tomographic image into a value smaller than the output value. At this time, in a case where the output value is equal to or lower than the threshold value, the controlling unit 40 may determine the driving amount by converting the output value into a value smaller than the output value. In addition, in a case where the output value is greater than the threshold value, the controlling unit 40 may determine a value smaller than the threshold value as the driving amount. Alternatively, the controlling unit 40 may converts the value output from the learned model receiving the obtained tomographic image into a value smaller than the output value, and in a case where the smaller value is equal to or lower than the threshold value, the controlling unit 40 may determine the smaller value as the driving amount. In addition, in a case where the smaller value is greater than the threshold value, the controlling unit 40 may determine the threshold value as the driving amount.

The processing then returns to step S42, where the controlling unit 40 performs the processing according to the flow as described above again.

In contrast, in a case where the number i of trials is determined to be equal to or greater than the maximum number of trial in step S48, the processing proceeds to exception processing in step S50. An example of the exception processing in step S50 will be described below.

An example of the exception processing may be processing for driving the coherence gate 64 to the rough-estimated position obtained in step S31. In addition, the processing may then cause the display unit 70 to display a message that prompts an examiner to perform a manual operation as necessary. In this case, the examiner can perform manual adjustment on the position of the coherence gate 64 as necessary by operating a coherence gate adjuster 207 in the imaging screen 200 illustrated in FIG. 2.

An example of the exception processing may be processing for driving the coherence gate 64 based on intensity values of the tomographic image. The example may be processing in which, for example, the coherence gate 64 is driven to the rough-estimated position, then an intensity value of a tomographic image within a reference range is obtained every time the coherence gate 64 is driven by a certain distance, and the coherence gate 64 is driven to a position at which the value is maximized. The reference range here can be set at, for example, a position in the tomographic image suitable for observation. In a case where there is no peak of changes in the intensity value within the reference range, the coherence gate 64 may be driven again in the same direction as that of driving to the rough-estimated position by the same distance.

In the exception processing, when driving the coherence gate 64 to the rough-estimated position, the controlling unit 40 may sequentially obtain the estimated distance in the processing in step S43 to determine whether the coherence gate 64 has moved closer to or away from the optimal position. From a result of the determination, a direction in which the coherence gate 64 is to be driven by the certain distance may be set at a direction in which the coherence gate 64 is moved close to the correct position. The certain distance here may be set at any value; for example, the certain distance can be set at the same value as that of the depth range of an imaged tomographic image.

Another example of the exception processing may be processing in which the coherence gate 64 is driven to an end of a range where the coherence gate 64 can be driven, then an intensity value of a tomographic image within a reference range is obtained every time the coherence gate 64 is driven by the certain distance, and the coherence gate 64 is driven to a position at which the value is maximized. The certain distance here may be set at any value; for example, the certain distance can be set at the entire range where the coherence gate 64 can be driven. In addition, the reference range here can be set at, for example, a position in the tomographic image suitable for observation.

An example of the exception processing may be processing for moving the coherence gate 64 to a center position of the range where the coherence gate 64 can be driven. The center position of the range where the coherence gate 64 can be driven here may be designed to be, for example, an optimal position for the coherence gate 64 for a fundus of an average diopter scale.

The controlling unit 40 can perform any one of the types of exception processing described above in step S50. After the exception processing is performed in step S50, the controlling unit 40 finishes the fine adjustment processing of coherence gate.

In a case where the adjustment is determined to be difficult to perform, the processing may proceed to the exception processing in step S50 before the number i of trials reaches the maximum number of trial in step S48. Examples of the case where the adjustment is difficult to perform include a case of a peculiar retina shape and a case where an image quality is poor under an apparatus condition. An example of how to determine whether the adjustment is difficult will be described below. First, after step S43, an estimated target position for the coherence gate 64 is calculated by subtracting the estimated distance from a current position of the coherence gate 64. In a case where the estimated target position fluctuates by a threshold value or greater for a predetermined number of times in a row, the controlling unit 40 determines that the adjustment is difficult. That is, the controlling unit 40 may perform the exception processing in a case where the number of times the fluctuation in the target position estimated by using the value output from the learned model receiving the obtained tomographic image (estimated distance) and the current position of the coherence gate 64 is equal to or greater than the threshold value reaches the predetermined number of times. At this time, the exception processing may include processing for driving the coherence gate 64 to the rough-estimated position described above. In addition, the exception processing may include processing for prompting an examiner to perform a manual operation. In addition, the exception processing may include processing for driving the coherence gate 64 based on intensity values of the tomographic image. The exception processing may include at least one of these types of processing. The threshold value here can be set, as an instability level, based on inference accuracy of the learned model or an inter-frame spacing of the training data and may be set at a value that is sufficiently large with respect to the inference accuracy or the inter-frame spacing. As an example, the threshold value can be set at a value that is three times the inference accuracy of the learned model or the inter-frame spacing of the training data. In addition, the predetermined number of times can be set to be smaller than the maximum number of trial; as an example, the predetermined number of times can be set to be about half the maximum number of trial. In a case where the adjustment is difficult, this enables the adjustment to be interrupted without waiting for the number of trials to reach the maximum number of trial, and thus a time taken until the processing proceeds to the exception processing can be shortened.

The distance by which the controlling unit 40 drives the coherence gate 64 in step S49 may be set according to an estimated distance that is obtained in the past. For example, the distance by which the coherence gate 64 is to be driven may be set to be equal to or lower than a previous estimated distance. This can reduce a risk that the coherence gate 64 is driven to a position far away from the correct position due to an erroneous estimation in a case where a blink specifically occurs during the adjustment.

In addition, in step S45, from an estimated distance or an estimated target position obtained in the past, the next estimated distance may be predicted. The next estimated distance can be predicted by regression analysis or the like on the estimated distance or the estimated target position obtained in the past. In a case where the estimated distance next obtained is significantly different from the prediction by a threshold value or greater, the obtained estimated distance may be determined to be an abnormal value. The threshold value here can be set, as an instability level, based on inference accuracy of the learned model or an inter-frame spacing of the training data and may be set at a value that is sufficiently large with respect to the inference accuracy or the inter-frame spacing. As an example, a value that is three times the inference accuracy of the learned model or the inter-frame spacing of the training data can be set as the threshold value. In a case where the obtained estimated distance is determined to be an abnormality value, the driving of the coherence gate 64 based on this estimated distance may not be performed, and the estimated distance may be obtained again in the next frame. At this time, the number i of trials may be incremented or may not be incremented. In a case where the estimated distance is determined to be an abnormality value for a predetermined number of times, the coherence gate 64 may be driven based on the last estimated distance. In the case where the estimated distance is determined to be an abnormality value for a predetermined number of times, the exception processing may be performed. The exception processing here may include processing for driving the coherence gate 64 to the rough-estimated position and processing for adjusting the coherence gate 64 based on a manual operation by an examiner or intensity values of the tomographic image. Alternatively, the coherence gate 64 may be driven based on the estimated distance predicted to be next obtained.

When an examiner determines that a manual adjustment is needed after the fine adjustment processing of coherence gate is finished, the manual adjustment may be performed by operating the coherence gate adjuster 207 in the imaging screen 200 illustrated in FIG. 2. In addition, after the fine adjustment processing of coherence gate is finished, the controlling unit 40 may store a current tomographic image as an optimal image. In a case where the adjustment of the coherence gate 64 is to be performed again, the driving amount of the driving motor 65 may be determined based on a difference between an estimated distance obtained from a tomographic image at the time and an estimated distance obtained from the optimal image.

Through the processing described above, the controlling unit 40 finishes the position adjustment processing of the coherence gate. After the coherence gate 64 is adjusted in the above-described manner, focus adjustment may be performed on the OCT as necessary. In this manner, the OCT apparatus can obtain the tomographic image 206.

As described above, an OCT apparatus according to the present embodiment that obtains a tomographic image of an eye to be examined by using combined light obtained by combining (a) return light from the eye to be examined irradiated with measurement light and (b) reference light includes an optical path length difference changing unit, a driving unit, a determining unit, and a controlling unit. The optical path length difference changing unit changes an optical path length difference between the measurement light and the reference light, and the driving unit drives the optical path length difference changing unit. The determining unit determines, using a learned model, a driving amount of the driving unit from the obtained tomographic image, and the controlling unit controls the driving unit using the determined driving amount. Here, the coherence gate 64 functions as an example of the optical path length difference changing unit, the controlling unit 40 functions as an example of the controlling unit and the determining unit, and the driving motor 65 function as an example of the driving unit.

More specifically, the determining unit uses the learned model to obtain an estimated distance from a current position to an optimal position of the optical path length difference changing unit from the obtained tomographic image, and determines the driving amount based on the estimated distance. In particular, the determining unit according to the present embodiment determines an estimated distance that is output from the learned model receiving the obtained tomographic image as the driving amount of the driving unit. The OCT apparatus according to the present embodiment can perform alignment using the optical path length difference changing unit in this manner, and the learned model can include a learned model for the alignment. The learned model may be a regression model or may be a classification model. In a case where the learned model is a regression model, the learned model can be obtained by supervised learning using a plurality of training data items that includes a plurality of tomographic images and continuous values obtained from different optical path length differences, each of which is an optical path length difference between the measurement light and the reference light. Here, the continuous values may be each an estimated distance to a target position of the optical path length difference changing unit, a driving amount of the driving unit for driving the optical path length difference changing unit to the target position, or the like.

With such a configuration, the OCT apparatus according to the present embodiment can drive the coherence gate 64 toward the optimal position based on the estimated distance obtained by using the learned model. Thus, the OCT apparatus can adjust the optical path length difference between the measurement light and the reference light with high accuracy.

In addition, the OCT apparatus can further include a selecting unit that selects a learned model that corresponds to the obtained tomographic image, the learned model being any one of a plurality of learned models that corresponds to a plurality of imaging conditions. Here, the controlling unit 40 can function as an example of the selecting unit. The determining unit may determine the driving amount of the driving unit from the obtained tomographic image using the selected learned model. Here, the obtained tomographic image may be a tomographic image that is obtained by performing correction processing on an image obtained by using the combined light. The correction processing may be one of processing for binarizing the image, processing for extracting some region of the image, processing for generating a tomographic image including both a real-image part and a mirror-image part, and processing for generating an image in which some image components are extracted from the tomographic image including both the real-image part and the mirror-image part.

The controlling unit may determine whether to drive the optical path length difference changing unit according to how long the estimated distance is. In this case, the controlling unit can perform exception processing in a case where the estimated distance is longer than the target distance. The exception processing can include processing for adjusting the optical path length difference changing unit based on a manual operation by an examiner or intensity values of the tomographic image.

Note that, in the present embodiment, the output of the learned model is taken as the estimated distance, and the estimated distance output from the learned model is set as the driving amount of the driving motor 65 to drive the coherence gate 64 next. In contrast, the output of the learned model may be the driving amount of the driving unit such as a number of revolutions of the driving motor 65 for driving the coherence gate 64. Here, the driving amount of the driving unit such as the number of revolutions of the driving motor 65 differs between apparatuses. Thus, for training data relating to the learned model, the driving amount of the driving unit obtained by using an OCT apparatus or a driving unit that is the same as or of the same type of an optical system of an OCT apparatus or a driving unit to be operated is to be used. In addition, in a case where the output of the learned model is to be used as the driving amount of the driving unit, a driving amount resulting from adding or subtracting a predetermined offset amount to or from the driving amount of the driving unit for driving the coherence gate 64 to the optimal position may be used as the training data. In this case, the entire retina can be easily made to be seen in the tomographic image without being turned down.

The output of the learned model may be a distance on the image or the number of pixels from a current position to a target position of a partial region of the tomographic image (retina region, etc.). In this case, for the training data, the distance or the number of pixels from the current position to the target position of the partial region of the tomographic image may be used. Note that, in this case, the controlling unit 40 needs to determine the driving amount of the driving unit from the distance or the number of pixels output from the learned model, for example, the number of revolutions of the driving motor 65. For example, the controlling unit 40 can determine the driving amount of the driving motor 65 by converting the distance on the image or the number of pixels output from the learned model into the number of revolutions of the driving motor 65 using a preset conversion table stored in a storage unit not illustrated.

Note that although a method for adjusting the coherence gate 64 to obtain a tomographic image of a fundus is described in the present embodiment, application of this adjusting method is not limited to fundi. For example, the adjusting method described above may be used to obtain a tomographic image of an anterior ocular segment.

Embodiment 2

Next, with reference to FIG. 13, Embodiment 2 of the present disclosure will be described. In the present embodiment, driving of the coherence gate 64 is controlled by using a learned model to track a retina in a tomographic image in a depth direction (Z direction) during imaging. The tracking here refers to correction in the Z direction such that the retina is seen appropriately in a case where the retina is not seen appropriately in the tomographic image because a position of a face deviates. Note that components of an OCT apparatus according to the present embodiment are the same as those of the OCT apparatus according to Embodiment 1 and thus will be denoted by the same reference numerals and will not be described. Processing by a controlling unit 40 according to the present embodiment will be described below mainly about difference from Embodiment 1.

Figure 13:
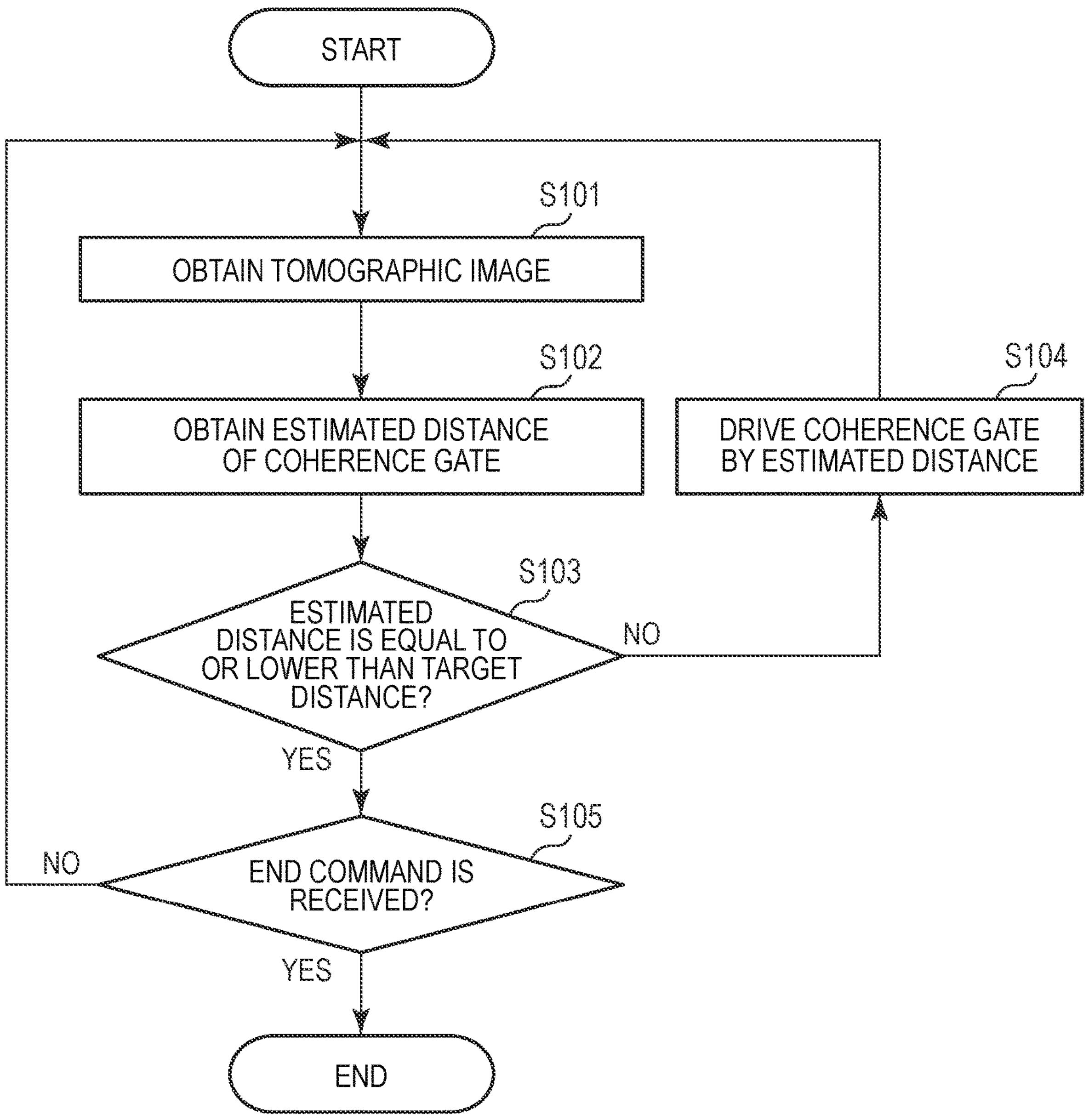
FIG. 13 illustrates an example of a flowchart of tracking processing according to Embodiment 2.

FIG. 13 is a flowchart of tracking processing according to the present embodiment. The processing is performed by the controlling unit 40. As the controlling unit 40 receives a start command, the processing is started. Examples of a timing for receiving the start command include a timing immediately after the adjustment of the coherence gate in Embodiment 1 is finished and a simultaneous timing with start of imaging for an OCT image or an OCTA image. Alternatively, the imaging screen 200 may be provided with a button for specifying ON/OFF of the tracking, and the start command for the tracking processing may be received as ON is specified by an examiner.

First, in step S101, the controlling unit 40 obtains tomographic images. The tomographic images may be tomographic images sequentially obtained in imaging. The tomographic images obtained by imaging are data having a density higher than a density of preview images that are obtained for alignment, and thus the tomographic images obtained here may be obtained by thinning the tomographic images obtained by imaging. By sequentially obtaining tomographic images in imaging and performing the following adjustment processing, an OCT image for which a coherence gate 64 is adjusted to an optimal position at each of positions in an imaging view angle. This enables a tomographic image that is satisfactory even at a peripheral portion in the imaging view angle to be obtained even in a case where a depth range of imaging of the apparatus is small or a case where a bend of the retina is large. In addition, a process of waiting a certain period of time may be provided before obtaining the tomographic images in step S101. The certain period of time may be set according to target specifications about a frame rate of the tracking.

The tomographic images obtained in step S101 may include a tomographic image obtained at a representative XY position that is set in advance, out of the tomographic images sequentially obtained in imaging. An example of the representative XY position is a position on a center line of the imaging view angle. Another example of the representative XY position is an XY position at which a C-scan is started. By obtaining a tomographic image only at the representative XY position and performing the following adjustment processing, an OCT image for which a position of the coherence gate 64 is kept constant in the imaging view angle can be generated.

The controlling unit 40 determines an image quality of the tomographic image obtained in step S101, and when the image quality is lower than a threshold value, the controlling unit 40 may not use the tomographic image but may obtain a tomographic image of the next frame. This can prevent a malfunction caused by a blink of a subject that specifically darkens a tomographic image. As an evaluation index for the image quality, for example, an intensity value of the tomographic image in a given range can be used.

Next, in step S102, the controlling unit 40 uses a learned model to obtain an estimated distance of the coherence gate 64 from the obtained tomographic image. This processing in step S102 of this flowchart may be the same processing as step S43 in Embodiment 1. The controlling unit 40 may determine, as the estimated distance obtained in step S102, a difference between an estimated distance obtained with the learned model from the tomographic image and an estimated distance obtained from the optimal image stored after the fine adjustment processing of coherence gate in Embodiment 1 is finished. The controlling unit 40 may correct the estimated distance based on the XY position of the tomographic image obtained in step S101.

In step S103, the controlling unit 40 determines whether the estimated distance obtained in step S102 is equal to or lower than a target distance. The target distance is an index of a distance for achieving a target adjustment accuracy and can be indicated by, for example, a deviation amount (distance) from an adjusted position as a target. The target distance may be set at, for example, 200 μm. Alternatively, the target distance may be determined based on an imaging range of a retina and the number of pixels of a tomographic image.

In a case where the estimated distance is determined not to be equal to or lower than the target distance, the processing proceeds to step S104. In step S104, the controlling unit 40 drives the coherence gate 64 by the estimated distance. The processing then returns to step S101, where the controlling unit 40 performs the processing according to the flow again.

In contrast, in a case where the estimated distance is determined to be equal to or lower than the target distance in step S103, the processing proceeds to step S105. In step S105, the controlling unit 40 determines whether an end command has been received. For example, the end command can be issued at the same time as the imaging is ended or when the imaging is interrupted. In a case where the end command has been received, the controlling unit 40 ends the tracking processing. In contrast, in a case where the end command has not been received, the controlling unit 40 returns the processing to step S101 and performs the processing according to the flow as described above.

The OCT apparatus according to the present embodiment performs the tracking using an optical path length difference changing unit in the above-described manner, and the learned model can include a learned model for the tracking. By obtaining an estimated distance of the coherence gate 64 from a tomographic image using a learned model as in the present embodiment, the tracking processing can be performed on various subjects with high accuracy.

Note that Embodiment 1 and Embodiment 2 may be combined together. In this case, the OCT apparatus can perform the alignment and the tracking with the optical path length difference changing unit. In addition, the learned model can separately include the learned model for the alignment and the learned model for the tracking.

Modifications according to at least one of Embodiment 1 and Embodiment 2 of the present disclosure will be described below.

Modification 1

Figure 14:
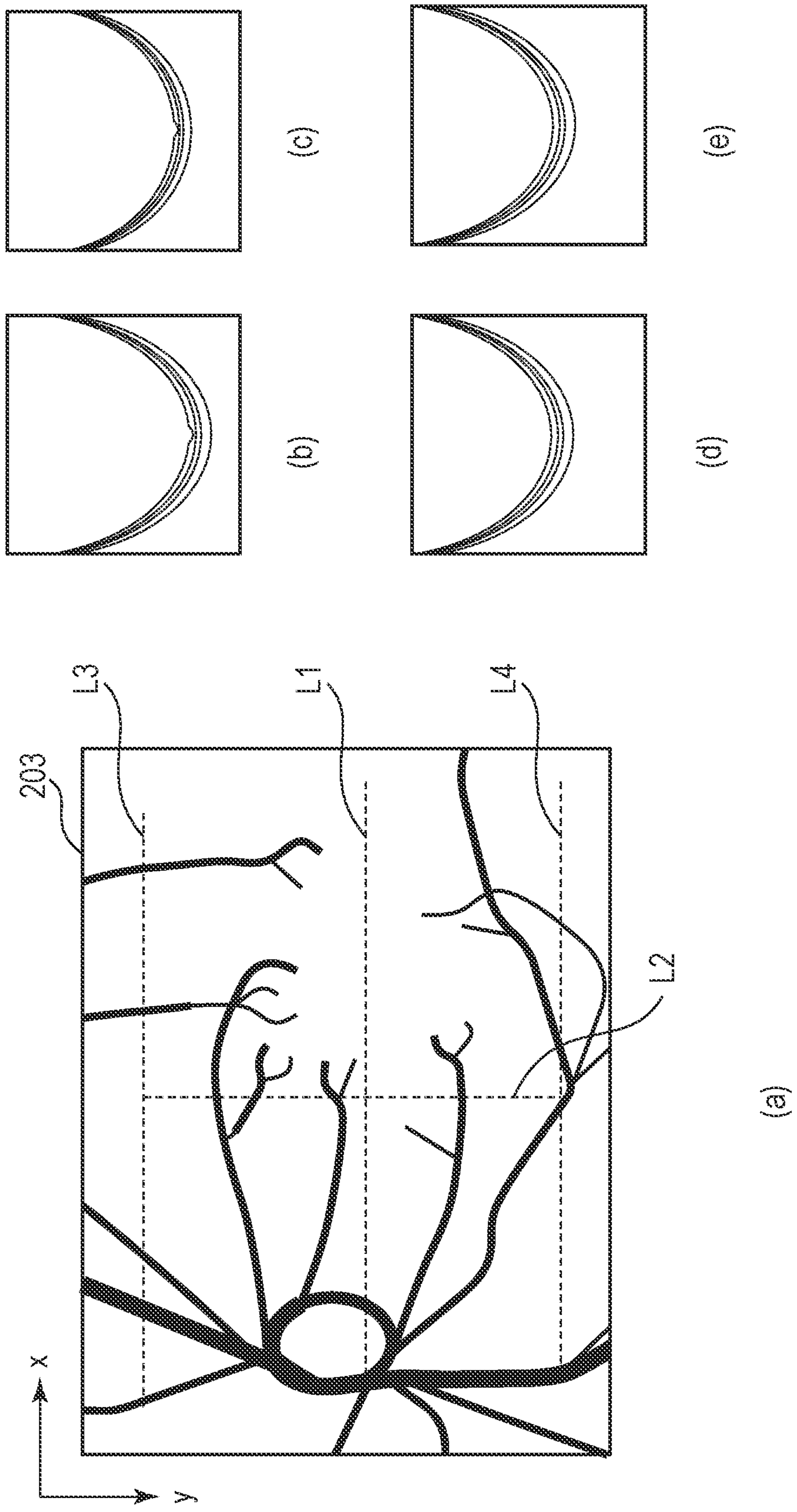
FIG. 14 illustrates an example of an SLO image and a plurality of tomographic images according to Modification 1.

In Modification 1 according to Embodiment 1 and Embodiment 2 of the present disclosure, the controlling unit 40 obtains an estimated distance from tomographic images obtained at a plurality of XY positions in step S43 or step S102. An example of obtaining the plurality of tomographic images will be described with reference to FIG. 14. An image (a) in FIG. 14 illustrates an example of the SLO image 203, where dotted lines L1, L2, L3 and L4 illustrate examples of the XY positions at which the tomographic images are obtained. The dotted lines L1 and L2 indicate center lines of the imaging view angle, and the dotted lines L3 and L4 indicate an example of positions of a peripheral view angle. Images (b), (c), (d) and (e) in FIG. 14 illustrate an example of tomographic images obtained at positions indicated by the dotted lines L1, L2, L3 and L4.

In an example of how to obtain an estimated distance from the plurality of tomographic images, the controlling unit 40 obtains estimated distances from the tomographic images illustrated in the images (b) to (e) in FIG. 14 using a learned model. At this time, when a DC component is on a vitreous body side, the controlling unit 40 determines a value that is estimated to be closest to a choroid out of the estimated distances obtained from the tomographic images as a final estimated distance. In contrast, when the DC component is on a choroid side, the controlling unit 40 determines a value that is estimated to be closest to a vitreous body out of the estimated distances obtained from the tomographic images as the final estimated distance. In this manner, tomographic images each having an image that is not turned up or down can be obtained at the positions indicated by the dotted lines L1, L2, L3 and L4 in imaging.

In another example of how to obtain an estimated distance from the plurality of tomographic images, the controlling unit 40 obtains estimated distances from the tomographic images illustrated in the images (b) to (e) in FIG. 14 using a learned model and determines an average value of the estimated distances as the final estimated distance. Alternatively, a value resulting from performing weighted averaging on the estimated distances obtained from the tomographic images illustrated in the images (b) to (e) in FIG. 14 may be determined as the final estimated distance. In this manner, tomographic images each having an image that is unlikely to be turned up or down can be obtained at the positions indicated by the dotted lines L1, L2, L3 and L4 in imaging.

As described above, a determining unit according to the present modification determines a driving amount of a driving unit using a plurality of values output from a learned model receiving a plurality of tomographic images obtained at different positions of an eye to be examined. With such a configuration, tomographic images each having an image that is unlikely to be turned up or down can be obtained at different positions of an eye to be examined in imaging.

XY positions for obtaining tomographic images are not limited to the positions indicated by dotted lines L1, L2, L3 and L4 illustrated in the image (a) in FIG. 14 and can be set at any positions. For example, the XY positions for obtaining tomographic images may be only the positions indicated by the dotted lines L1 and L2 or may be set at other positions.

Note that the pattern for scanning illustrated in the image (a) in FIG. 14 to perform the fine adjustment on the coherence gate 64 in step S33 is merely an example and does not limit patterns for scanning. Depending on a scanning pattern in imaging, the controlling unit 40 may change a size and a shape of a scanning pattern and the number of samples for performing the fine adjustment on the coherence gate 64, as appropriate. In the machine learning, one learned model may be provided so that the estimated distance can be calculated for various scanning patterns, or different learned models may be provided for scanning patterns of different sizes for example. A learned model may be provided for a tomographic image obtained at each of the positions, or a single model may be applied commonly to the tomographic images obtained at the positions.

One combined image resulting from joining tomographic images obtained at two or more XY positions together may be used as input data for a machine learning model. An example of how to generate the combined image is arranging the tomographic images laterally or longitudinally. Another example of how to generate the combined image is adding or averaging intensity values of each tomographic image to generate one image.

Alternatively, tomographic images obtained at two or more XY positions may be input, and feature quantities obtained from the tomographic images in the middle of learning may be combined. For example, the feature quantities of the tomographic images can be combined in or immediately before a fully connected layer. How to combine the feature quantities obtained from the tomographic images in the middle of the learning is not limited to the above, and the feature quantities can be combined by various methods.

Modification 2

In Modification 2 according to Embodiment 1 and Embodiment 2 of the present disclosure, the controlling unit 40 obtains an estimated distance from tomographic images obtained at a plurality of Z positions in step S43 or step S102. In the present modification, the controlling unit 40 obtains tomographic images at the plurality of Z positions when the coherence gate 64 is driven in step S32, step S47, step S49, or the like.

Figure 15:
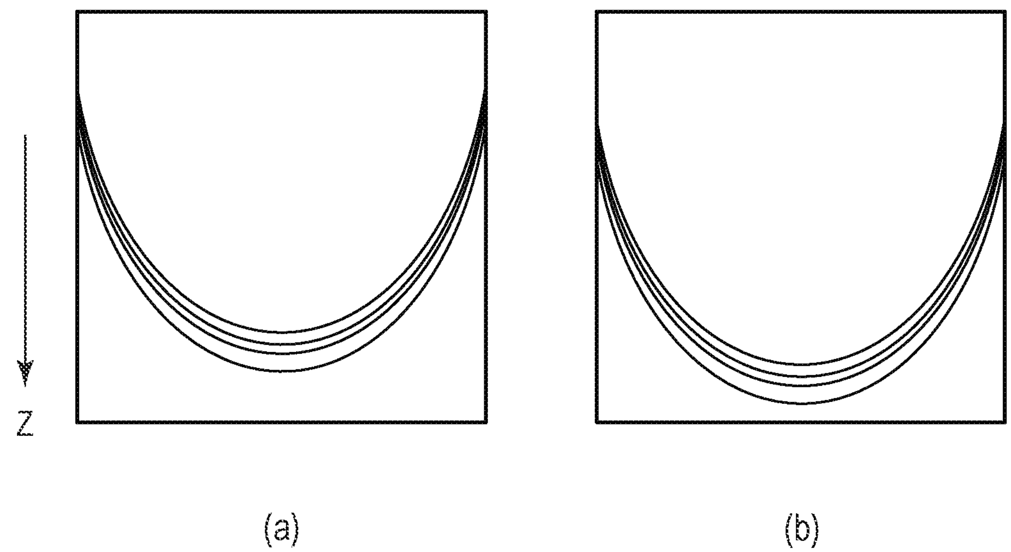
FIG. 15 illustrates an example of a plurality of tomographic images according to Modification 2.

As an example, a case where an estimated distance is obtained from tomographic images obtained at two Z positions will be described with reference to FIG. 15. Images (a) and (b) in FIG. 15 illustrate an example of tomographic images that are obtained while the coherence gate 64 is driven. The image (b) in FIG. 15 is a tomographic image obtained when the driving of the coherence gate 64 is finished, and the image (a) in FIG. 15 is a tomographic image obtained in a frame previous to a frame for obtaining the image (b). Note that an interval of the frames for obtaining the tomographic images can be set optionally. For example, by adjusting a driving speed of the coherence gate 64 and a sampling time, an inter-frame spacing can be set such that the coherence gate 64 is positioned at about 500 μm intervals.

Using a learned model, the controlling unit 40 obtains estimated distances lc1 and lc2 from the tomographic images illustrated in the images (a) and (b) in FIG. 15, respectively. The controlling unit 40 checks a direction D1 toward an optimal position of the coherence gate 64 based on a sign of the estimated distance lc2. In addition, the controlling unit 40 determines whether the coherence gate 64 has moved closer to or away from the optimal position by the driving of the coherence gate 64 as described above, based on a sign of Δlc=lc2−lc1. Based on a result of this determination, the controlling unit 40 determines a direction D2 in which the coherence gate 64 is to be driven next so that the coherence gate 64 is moved close to the optimal position.

When the direction D1 and the direction D2 match, the controlling unit 40 then drives the coherence gate 64 in the direction D1 by the estimated distance lc2. In contrast, when D1 and D2 do not match, the controlling unit 40 then drives the coherence gate 64 in the direction D2 by a predetermined distance and obtains an estimated distance from tomographic images again. The predetermined distance here can be set at, for example, a depth range of the tomographic images.

Figure 16:
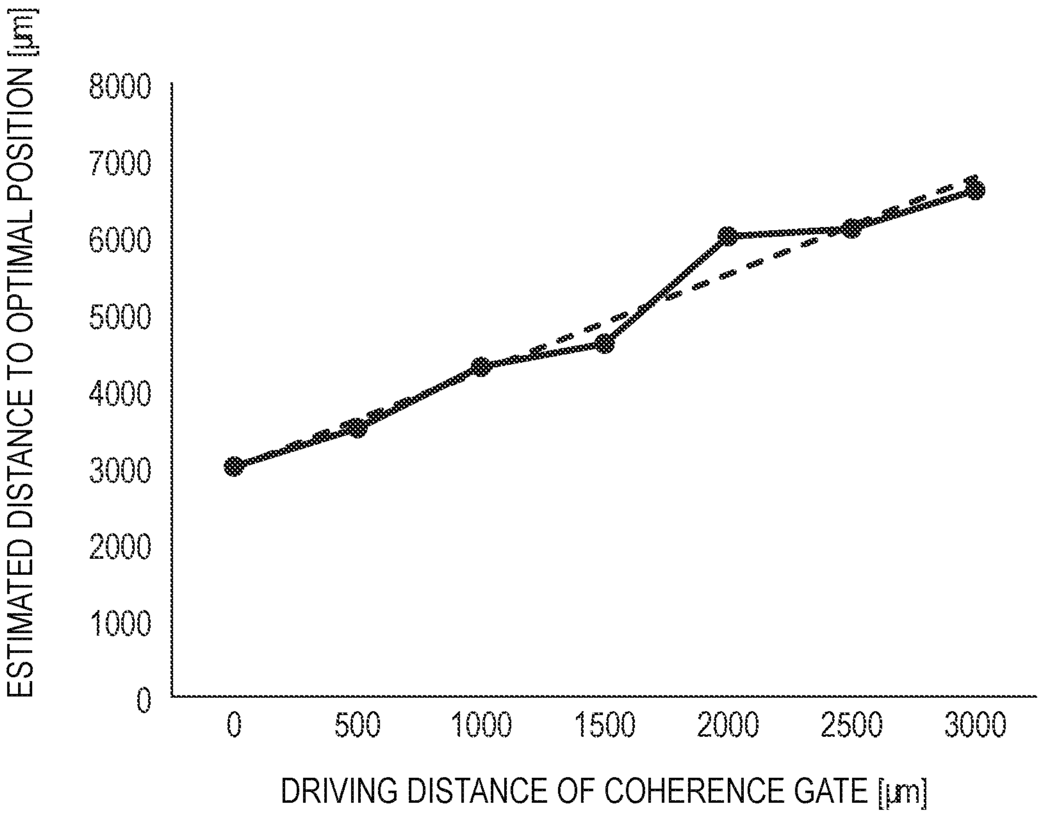
FIG. 16 illustrates an example of changes in estimated distance according to Modification 2.

Although an example of obtaining an estimated distance from tomographic images obtained at two Z positions is described in the present modification, the number of the Z positions is not limited to two, and the same processing may be performed at a plurality of Z positions as larger as three or more. Here, FIG. 16 illustrates an example of results of obtaining estimated distances at three or more Z positions of the coherence gate 64. In FIG. 16, a line graph of solid lines indicates estimated distances obtained actually, and a dotted line is an approximate straight line of the line graph. In this case, based on whether a slope of the approximate straight line is positive or negative, the controlling unit 40 can determine whether the coherence gate 64 has moved closer to or away from the optimal position by being driven. Based on a result of this determination, the controlling unit 40 can determine the direction D2 in which the coherence gate 64 is to be driven next so that the coherence gate 64 is moved close to the optimal position and perform the same processing as the above.

In the present modification, the approximate straight line illustrated in FIG. 16 may be created in the middle of the adjustment, and an estimated distance to be obtained next may be predicted from the approximate straight line. In a case where the estimated distance next obtained is significantly different from the prediction by a threshold value or greater, the obtained estimated distance may be determined to be an abnormal value. The threshold value here can be set, as an instability level, based on inference accuracy of the learned model or an inter-frame spacing of the training data and may be set at a value that is sufficiently large with respect to the inference accuracy or the inter-frame spacing. As an example, the threshold value can be set at a value that is three times the inference accuracy of the learned model or the inter-frame spacing of the training data. In a case where the obtained estimated distance is determined to be an abnormality value, the driving of the coherence gate 64 based on this estimated distance may not be performed, and the estimated distance may be obtained again in the next frame. In a case where the estimated distance is determined to be an abnormality value for a predetermined number of times, the coherence gate 64 may be driven based on the last estimated distance. In the case where the estimated distance is determined to be an abnormality value for a predetermined number of times, the exception processing may be performed. The exception processing may include processing for driving the coherence gate 64 to a rough-estimated position and processing for adjusting the coherence gate 64 based on a manual operation by an examiner or intensity values of the tomographic image. Alternatively, the coherence gate 64 may be driven based on the estimated distance predicted to be next obtained.

As described above, a determining unit according to the present modification determines a driving amount of a driving unit using a plurality of values output from a learned model receiving a plurality of tomographic images obtained for different optical path length differences. With such a configuration, a risk that the coherence gate 64 is driven in an opposite direction to a correct direction due to an error in the estimation or a risk that the coherence gate 64 is driven to a position different from a correct position due to erroneous estimation can be reduced.

Modification 3

In Modification 3 according to Embodiment 1 and Embodiment 2 of the present disclosure, the controlling unit 40 obtains an estimated distance of the coherence gate 64 using a plurality of learned models in step S43 or step S102. The plurality of learned models can be generated by combining various kinds of input data, machine learning algorithms, and output data.

Examples of the input data for the learned models that can be included in the controlling unit 40 include tomographic images, binarized images of the tomographic images, and images resulting from extracting parts of the tomographic images. Algorithms for the machine learning models that can be included in the controlling unit 40 include, as described above, algorithms using a neural network or a decision tree and algorithms for various methods such as a support vector machine. Examples of the output data for the machine learning models that can be included in the controlling unit 40 include estimated distances of the coherence gate 64, classification classes of the estimated distances, and directions from current positions to optimal positions of the coherence gate 64. By combining the above, a plurality of machine learning models can be provided.

Based on output results from such a plurality of machine learning models, the controlling unit 40 can determine a final estimated distance. For example, the controlling unit 40 can determine the final estimated distance by averaging estimated distances obtained from the different machine learning models.

Modification 4

In Embodiment 1 and Embodiment 2, the driving amount of the driving motor 65 is determined by inputting tomographic images obtained by the OCT apparatus into a learned model. However, images input into the learned model is not limited to tomographic images. In Modification 4 according to Embodiment 1 and Embodiment 2 of the present disclosure, a driving amount of a driving motor 65 is determined by inputting fundus observation images into a learned model. Examples of the fundus observation images include fundus photographs and SLO images obtained with visible light or infrared light. The OCT apparatus described in Embodiments 1 and 2 can obtain SLO images by using the SLO optical system 80. The OCT apparatus may include, for example, a fundus camera for imaging a fundus photograph.

For the present modification, the fact that deviation of an eye (retina) from an optimum Z position appears in a form of defocus in a fundus observation image is utilized. Alternatively, the fact that brightness of an SLO image changes as a result of defocus may be utilized for the present modification. For example, assume that a position of a coherence gate 64 is moved in coordination with a position of a focus lens 58. In this case, in a case where defocus occurs in a fundus observation image corresponding to the position of the focus lens 58, a distance by which the coherence gate 64 is to be moved can be estimated according to an amount of the defocus. Thus, a learned model according to the present modification is generated by learning combinations of fundus observation images obtained in a focused state and a defocused state and deviations of the coherence gate 64 for the fundus observation images from an optimal position. Note that an apparatus configuration of the apparatus for obtaining the fundus observation images used for the learning can be the same or the same type of an apparatus configuration for obtaining fundus observation image in an OCT apparatus to be operated.

Combined images of tomographic images and fundus observation images may be input into the learned model. The learned model here is generated by learning combinations of the combined images of tomographic images and fundus observation images and deviations of the coherence gate 64 for the combined images from the optimal position. A combined image as an example here can be generated by arranging a tomographic image and a fundus observation image to generate one image. Note that, in this case, the position of the coherence gate 64 may not be moved in coordination with the position of the focus lens 58.

Alternatively, the driving amount of the driving motor 65 may be finally determined by combining an estimated distance obtained by inputting a tomographic image into the learned model and estimated distance obtained by inputting a fundus observation image into the learned model. Examples of how to combine the estimated distance obtained from a tomographic image and the estimated distance obtained from a fundus observation image include averaging these estimated distances. Note that, also in this case, the position of the coherence gate 64 may not be moved in coordination with the position of the focus lens 58.

Alternatively, the tomographic image and the fundus observation image may be input, and feature quantities obtained from the images in the middle of learning may be combined. For example, the feature quantities of the images can be combined in or immediately before a fully connected layer. How to combine the feature quantities obtained from the images in the middle of the learning is not limited to the above, and the feature quantities can be combined by various methods.

Modification 5

In Modification 5 according to Embodiment 1 of the present disclosure, immediately before the fine adjustment is performed on a coherence gate 64 in step S33, adjustment is performed such that at least part of a retina is seen in a tomographic image. In the present modification, during driving the coherence gate 64 in step S32, a controlling unit 40 obtains tomographic images at predetermined time intervals and obtains intensity values of the tomographic images within a reference range.

The controlling unit 40 obtains a tomographic image immediately before performing the fine adjustment on the coherence gate 64 in step S33 and determines whether an intensity condition is satisfied. At this point, the controlling unit 40 can analyze the obtained tomographic image by any well-known method to obtain a frequency distribution of the tomographic image. Here, the intensity condition is for determining whether at least part of the retina to be observed is seen in a current tomographic image. As an example of the intensity condition, whether the top 5% of intensity values in the frequency distribution of the tomographic image are equal to or greater than a threshold value can be set. As another example of the intensity condition, whether at least one of indices such as a variance, a standard deviation, a skewness, and kurtosis of the frequency distribution of the tomographic image is equal to or greater than a threshold value can be set. These threshold values can be set based on intensity values of a retina portion in a tomographic image imaged after appropriate adjustment, a variance, a standard deviation, a skewness, a kurtosis of a frequency distribution of the tomographic image, or the like.

The controlling unit 40 may use a learned model to determine whether a tomographic image satisfies the intensity condition. This machine learning model can be generated by learning a large number of pairs of tomographic images and results of checking whether the intensity condition is satisfied.

Alternatively, the controlling unit 40 may obtain a tomographic image a plurality of times at predetermined frame intervals and may determine whether the intensity condition is satisfied for a tomographic image having a highest intensity value out of the tomographic images. In this manner, a malfunction caused by a blink of a subject that darkens a tomographic image can be prevented. As an example, the controlling unit 40 can obtain a tomographic image three times at an interval of 100 milliseconds.

Figure 17:
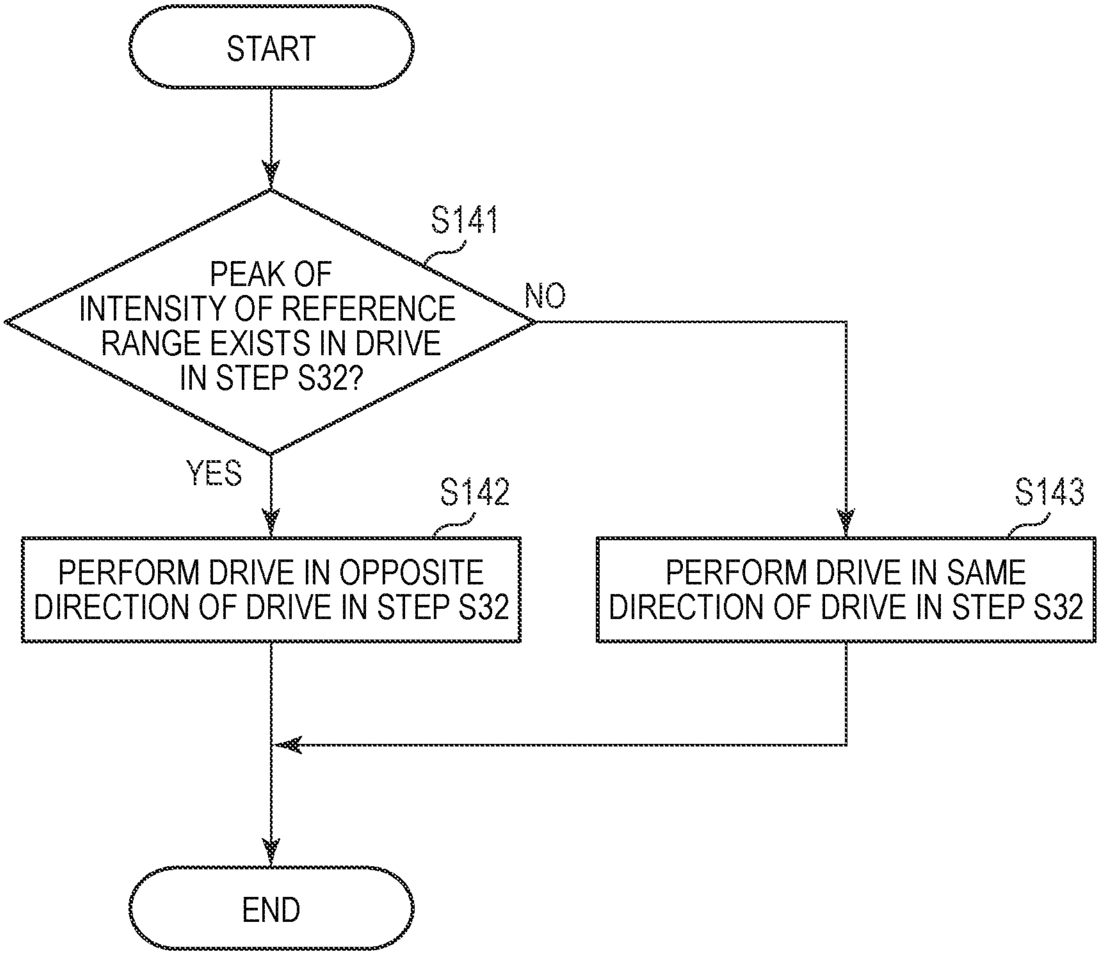
FIG. 17 illustrates an example of a flowchart of correction processing of a coherence gate according to Modification 5.

In a case where the intensity condition is not satisfied, the controlling unit 40 can perform correction processing of a coherence gate. With reference to FIG. 17, the correction processing of a coherence gate according to the present modification will be described.

First, in step S141, the controlling unit 40 refers to a change in intensity value obtained during the driving of the coherence gate in step S32 and determines whether there is a peak being equal to or greater than a threshold value. The threshold value here can be set at a value that can be considered to be sufficiently large with respect to a noise level.

In a case where it is determined that there is a peak being equal to or greater than the threshold value, the processing proceeds to step S142. In step S142, the controlling unit 40 drives the coherence gate 64 in an opposite direction to the direction of driving the coherence gate in step S32. As an example, the controlling unit 40 can drive coherence gate 64 to a position of the coherence gate 64 at which the intensity value reaches the peak. After the driving of the coherence gate 64 in step S142 is finished, the controlling unit 40 finishes the correction processing of the coherence gate according to the present modification and causes the processing to proceed to step S33.

In contrast, in a case where it is determined that there is no peak being equal to or greater than the threshold value, the processing proceeds to step S143. In step S143, the controlling unit 40 drives the coherence gate 64 in the same direction as the direction of driving the coherence gate in step S32. The driving amount of the driving motor 65 here may be set at any value; for example, the driving amount of the driving motor 65 can be set at the same value as the depth range of an imaged tomographic image. After the driving of the coherence gate 64 in step S143 is finished, the controlling unit 40 finishes the correction processing of the coherence gate according to the present modification and causes the processing to proceed to step S33.

As described above, by causing the processing to proceed to step S33 in a state where at least part of a retina is seen in a tomographic image, the fine adjustment can be performed on the coherence gate 64 more stably.

Modification 6

In Modification 6 according to Embodiment 1 of the present disclosure, immediately before whether the estimated distance is equal to or lower than the target distance is determined in step S45, whether a retina is seen in a tomographic image is determined based on the estimated distance. A blink or the like is thereby detected.

In the present modification, tomographic images in which no retina is seen are included in training data. The tomographic images in which no retina is seen are given a ground truth label of the same estimated distance or ground truth labels of estimated distances within a common limitative range. The tomographic images in which no retina is seen may be obtained by performing imaging under a condition that causes an eye to be examined not to be seen in the tomographic images. At this time, the tomographic images may be given a common ground truth label.

Figure 18:
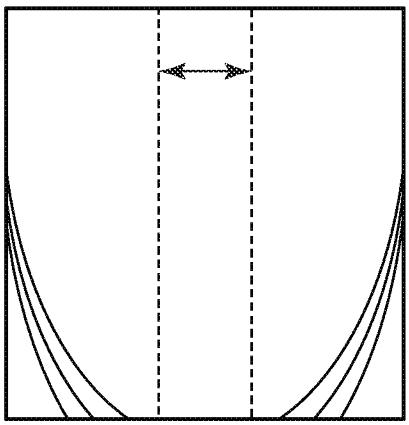
FIG. 18 illustrates an example of tomographic images of a wide angle of view and a narrow angle of view according to Modification 6.
Figure 18:
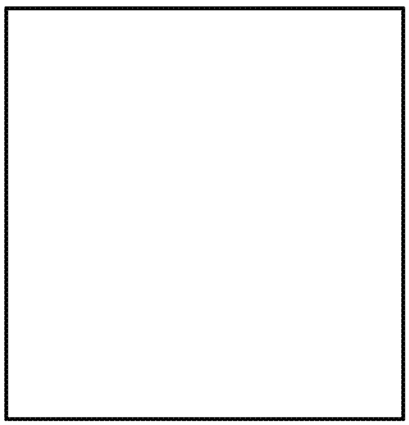

FIG. 18 illustrates an image of a wide angle of view (the image (a) in FIG. 18) and an image of a narrow angle of view (the image (b) in FIG. 18) obtained when the coherence gate 64 is set at some position. The image (b) in FIG. 18 is an image imaged with an angle of view illustrated as an inside between dotted lines in the image (a) in FIG. 18. As described above, a tomographic image may be obtained at a position of the coherence gate 64 that causes the retina to be seen when imaged with a wide angle of view (the image (a) in FIG. 18) and causes the retina not to be seen when imaged with a narrow angle of view (the image (b) in FIG. 18). In this case, tomographic images in which no retina is seen are given labels of estimated distances within a certain range.

In the present modification, the controlling unit 40 subtracts the estimated distance from a current position of the coherence gate 64 to calculate an estimated target position for the coherence gate 64. The controlling unit 40 then compares a previous estimated target position and the current estimated target position. In a case where a difference between the previous estimated target position and the current estimated target position is equal to or greater than a threshold value, and the current estimated distance is within the range of labels that are given because no retina is seen as described above, the current tomographic image is determined to be with no retina seen. Here, the threshold value for the difference between the previous estimated target position and the current estimated target position can be set, as an instability level, based on inference accuracy of the learned model or an inter-frame spacing of the training data and may be set at a value that is sufficiently large with respect to the inference accuracy or the inter-frame spacing. As an example, the threshold value can be set at a value that is three times the inference accuracy of the learned model or the inter-frame spacing of the training data. However, the value of the threshold value is not limited to the above and can be set at any value. Alternatively, whether a retina is seen in a tomographic image may be determined based on, in place of the comparison between the previous estimated target position and the current estimated target position, whether a difference value between the previous estimated distance and the current estimated distance is sufficiently large with respect to a recent driving amount of the coherence gate 64.

In a case where the current tomographic image is determined to be with no retina seen, the coherence gate 64 is not driven, and the processing returns to step S42. At this time, a certain period of waiting time may be provided before the processing returns to step S42. This waiting time can be set at, for example, 100 ms, and the provision of this waiting time increases a possibility that a blink has already ended at the next estimation. The waiting time here can be set at any value.

The determination as to whether a retina is seen in the tomographic image may be performed immediately before step S44, and in this case, the number i of trials is not incremented.

Modification 7

In Modification 7 according to Embodiment 1 of the present disclosure, a case where a coherence gate 64 has been driven in an opposite direction to a direction toward a correct position is detected based on an estimated distance immediately after step S43 or immediately after step S44. In particular, since there is a case where images obtained at positions of the coherence gate 64 away from each other have similar image structures as with the images (a) and (e) in FIG. 6, there is concern about occurrence of erroneous estimation in step S43 that may cause the coherence gate 64 to be driven in the opposite direction to the direction toward the correct position. In addition, driving the coherence gate 64 in the opposite direction to the direction toward the correct position results in a decrease in coherence due to being away from a DC component, which can cause a retina not to be seen in an image. In a case where images in which no retina is seen are learned with some ground truth labels as in Modification 6, a certain estimated distance is output while no retina is seen in images. In a case where this estimated distance is in the opposite direction to the direction toward the correct position, the coherence gate 64 continues to move in the opposite direction from the correct position. As countermeasures against these problems, the detection described in the present modification is effective.

First, an estimated target position for the coherence gate 64 is calculated by subtracting the estimated distance from a current position of the coherence gate 64. In a case where the estimated target position fluctuates by a threshold value or greater for a predetermined number of times in a row and continues to be away from a reference position of the coherence gate 64, the controlling unit 40 determines that the coherence gate 64 is being driven in the opposite direction to the direction toward the correct position. That is, the controlling unit 40 may determine that the coherence gate 64 is being driven in a direction away from the correct position in a case where the number of times the fluctuation in the target position estimated by using the value output from the learned model receiving the obtained tomographic image (estimated distance) and the current position of the coherence gate 64 satisfies a condition of being equal to or greater than the threshold value reaches the predetermined number of times. The reference position of the coherence gate 64 here may be a representative value such as a position of the coherence gate 64 optically calculated for an average eye to be examined and an average value resulting from adjustments of the coherence gate 64 performed on many eyes to be examined can be used. In addition, the predetermined number of times here is set from the number of frames equivalent to a time period that is sufficiently large with respect to a time taken by an average blink so that the driving in the opposite direction is not confused with, for example, a blink. For example, in a case where an interval between every frame is 100 ms, the predetermined number of times can be set at five as an example. The value is not limited to the above and can be set at any other values. In addition, the threshold value for the fluctuation here can be set, as an instability level, based on inference accuracy of the learned model or an inter-frame spacing of the training data and may be set at, for example, a value that is sufficiently large with respect to the inference accuracy or the inter-frame spacing. As an example, the threshold value can be set at a value that is three times the inference accuracy of the learned model or the inter-frame spacing of the training data. However, the value of the threshold value is not limited to the above and can be set at any value.

In a case where the coherence gate 64 is being driven in the opposite direction to the direction toward the correct position, the controlling unit 40 drives the coherence gate 64 to a position to which the coherence gate 64 moves away from the rough-estimated position by a predetermined distance in an opposite direction to a direction in which the coherence gate 64 is being driven. The predetermined distance here can be set at, for example, a depth range of imaging the tomographic images. In this manner, in a case where a driving direction is erroneously estimated because images obtained at positions of the coherence gate 64 away from each other have similar image structures or in a case where a tomographic image is so dark that a certain estimated distance is continuously output due to being away from a DC component, the coherence gate 64 being driven in the opposite direction can be stopped in the middle of the driving and can be brought within a range within which an accuracy of the estimation ameliorates.

In a case where the current position is away from the reference position for a predetermined number of times in a row, the controlling unit 40 may determine that the coherence gate 64 is being driven in the opposite direction to the direction toward the correct position. However, this method raises a possibility that the coherence gate 64 is erroneously determined to be driven in the opposite direction when the correct position is away from the reference position. Thus, by making the determination based on the fluctuations in estimated target position as described above, a possibility of such an erroneous determination can be decreased.

Other Modifications

In the embodiments and modifications described above, a case where the coherence gate 64 is driven as an example of the optical path length difference changing unit that changes a difference in optical path length between the measurement light and the reference light. In contrast, another example of the optical path length difference changing unit is an optical head including the optical system illustrated in FIG. 1, and the optical path length difference between the measurement light and the reference light may be changed by driving the optical head in place of the coherence gate 64. In this case, a driving amount of the optical head can be determined by using a learned model from a tomographic image of an eye to be examined. The learned model here can be generated by learning tomographic images of eyes to be examined and relative positions (or distances from optimal positions) of the optical head to eyes to be examined in combination. Note that any other component or mechanism that can change the optical path length difference between the measurement light and the reference light may be used as the optical path length difference changing unit. For example, the optical path length difference changing unit may include any mirror that is disposed on an optical path of the measurement light for changing an optical path length of the measurement light.

In addition, training data for the various learned models is not limited to data obtained by using an OCT apparatus itself with which imaging is to be actually performed and may be data or the like obtained by using an OCT apparatus of the same model or an OCT apparatus of the same type according to a desired configuration.

The various learned models according to the embodiments and modifications described above can be provided in the controlling unit 40. The learned models may be implemented as, for example, a software module to be executed by a processor such as a CPU, an MPU, a GPU and an FPGA or may be implemented as a circuit fulfilling a particular function such as an ASIC. These learned models may be provided in an apparatus for a separate server connected to the controlling unit 40. In this case, the controlling unit 40 can use a learned model by being connected to the server or the like including the learned model over any network such as the Internet. Here, the server including the learned model may be, for example, a cloud server, a fog server, or an edge server. Note that in a case where a network in a facility, a site including a facility, an area including a plurality of facilities, or the like is configured to be capable of wireless communication, a reliability of the network may be improved by, for example, using a radio wave within a dedicated wavelength band that is allocated to the facility, site, or area. The network may be configured by a wireless communication that enables high speed, large capacity, low latency, and massive concurrent connections.

The embodiments and the modifications described above can be combined as appropriate without departing from the scope of the present disclosure. For example, the controlling unit 40 can include both the learned model for the alignment of the coherence gate 64 described in Embodiment 1 and the learned model for the tracking of the coherence gate 64 described in Embodiment 2.

According to at least one of the embodiments and modifications described above of the present disclosure, an optical path length difference between measurement light and reference light can be adjusted with high accuracy in optical coherence tomography.

Other Examples

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

At this time, examples of the processor or circuit may include a central processing unit (CPU), a microprocessing unit (MPU), a graphics processing unit (GPU), an application specific integrated circuit (ASIC), or a field programmable gateway (FPGA). Further, examples of the processor or circuit may include a digital signal processor (DSP), a data flow processor (DFP) or a neural processing unit (NPU).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2020-208772, filed Dec. 16, 2020, and Japanese Patent Application No. 2021-109337, filed Jun. 30, 2021, which are hereby incorporated by reference herein in their entirety.

What is claimed is:

1. An optical coherence tomography apparatus that obtains a tomographic image of an eye to be examined by using combined light obtained by combining (a) return light from the eye to be examined irradiated with measurement light and (b) reference light, the optical coherence tomography apparatus comprising:

an optical path length difference changing unit arranged to change an optical path length difference between the measurement light and the reference light;

a driving unit arranged to drive the optical path length difference changing unit; and a controlling unit configured to control the driving unit using a driving amount of the driving unit, wherein the driving amount is determined using a plurality of values output from a learned model by inputting to the learned model a plurality of tomographic images obtained for different optical path length differences.

2. An optical coherence tomography apparatus according to claim 1, further comprising a determining unit configured to determine the driving amount and configured using a processor of the optical coherence tomography apparatus or an external processor communicably connected to the optical coherence tomography apparatus, wherein the determining unit performs one of:

(1) determining, as the driving amount, a value obtained using the plurality of values that are output from the learned model by inputting to the learned model the plurality of tomographic images; and (2) determining the driving amount by converting the value obtained using the plurality of values that are output from the learned model by inputting to the learned model the plurality of tomographic images into a value smaller than the obtained value.

3. An optical coherence tomography apparatus according to claim 1, further comprising a determining unit configured to determine the driving amount and configured using a processor of the optical coherence tomography apparatus or an external processor communicably connected to the optical coherence tomography apparatus, wherein the determining unit performs one of:

(1) determining the driving amount by, in a case where a value obtained using the plurality of values that are output from the learned model by inputting to the learned model the plurality of tomographic images is equal to or lower than a threshold value, converting the obtained value into a value smaller than the obtained value; and (2) converting the value obtained using the plurality of values output from the learned model by inputting to the learned model the plurality of tomographic images into a value smaller than the obtained value, and determining the smaller value as the driving amount in a case where the smaller value is equal to or lower than the threshold value.

4. An optical coherence tomography apparatus according to claim 2, wherein the determining unit determines the driving amount by adding an offset amount corresponding to an imaging view angle included in an imaging condition to the smaller value.

5. An optical coherence tomography apparatus according to claim 1, further comprising:

a determining unit configured to determine the driving amount and configured using a processor of the optical coherence tomography apparatus or an external processor communicably connected to the optical coherence tomography apparatus, and a selecting unit configured to select a learned model that corresponds to the obtained tomographic image, the learned model being any one of a plurality of learned models that corresponds to a plurality of imaging conditions, wherein the determining unit determines, using the selected learned model, the driving amount from the plurality of tomographic images.

6. An optical coherence tomography apparatus according to claim 1, wherein the optical coherence tomography apparatus performs at least one of alignment and tracking with the optical path length difference changing unit, and wherein the learned model includes a learned model for the alignment and a learned model for the tracking, separately.

7. An optical coherence tomography apparatus according to claim 1, wherein each of the plurality of tomographic images is a tomographic image that is obtained by performing correction processing on an image obtained by using the combined light, and wherein the correction processing includes one of (1) processing for binarizing the image, (2) processing for extracting some region of the image, (3) processing for generating a tomographic image including both a real-image part and a mirror-image part, and (4) processing for generating an image in which some image components are extracted from the tomographic image including both the real-image part and the mirror-image part.

8. An optical coherence tomography apparatus according to claim 1, wherein a target position of the optical path length difference changing unit that is a target for adjusting the optical path length difference can be adjusted by an examiner.

9. An optical coherence tomography apparatus according to claim 1, wherein the learned model is a regression model, and is obtained by supervised learning using a plurality of training data that includes a plurality of tomographic images and continuous values obtained for different optical path length differences each of which is an optical path length difference between the measurement light and the reference light.

10. An optical coherence tomography apparatus according to claim 1, wherein determining the driving amount and controlling the driving unit are performed after the optical path length difference changing unit is driven by using a result of focus adjustment for at least one of an SLO image, an anterior segment image, and a fundus photograph.

11. An optical coherence tomography apparatus according to claim 10, wherein the controlling unit performs exception processing in a case where the number of times that a fluctuation in a target position estimated by using (1) a value obtained using the plurality of values output from the learned model by inputting to the learned model the plurality of tomographic images and (2) a current position of the optical path length difference changing unit is equal to or greater than a threshold value reaches a predetermined number of times, the exception processing including processing for driving the optical path length difference changing unit to a position to which the optical path length difference changing unit is driven by using the result of the focus adjustment.

12. An optical coherence tomography apparatus according to claim 1, wherein the controlling unit performs exception processing in a case where the number of times that a fluctuation in a target position estimated by using (1) a value obtained using the plurality of values output from the learned model by inputting to the learned model the plurality of tomographic images and (2) a current position of the optical path length difference changing unit is equal to or greater than a threshold value reaches a predetermined number of times, the exception processing including at least one of (a) processing for prompting an examiner to perform a manual operation and (b) processing for driving the optical path length difference changing unit based on an intensity value of the tomographic image.

13. An optical coherence tomography apparatus according to claim 1, wherein the controlling unit determines that the optical path length difference changing unit is driven in a direction away from a correct position in a case where the number of times that a fluctuation in a target position estimated by using (1) a value obtained using the plurality of values output from the learned model by inputting to the learned model the plurality of tomographic images and (2) a current position of the optical path length difference changing unit is equal to or greater than a threshold value reaches a predetermined number of times.

14. An optical coherence tomography apparatus according to claim 1, wherein as the learned model, any one of a plurality of learned models that corresponds to a plurality of target positions for the optical path length difference changing unit is selected, the plurality of target positions each being a target position that is a target for adjusting the optical path length difference.

15. An optical coherence tomography apparatus according to claim 1, wherein as the learned model, a learned model that corresponds to a vitreous body mode is selected in a case where the vitreous body mode is selected, the vitreous body mode being one of imaging modes included in an imaging condition, and wherein as the learned model, a learned model that corresponds to a choroid mode is selected in a case where the choroid mode is selected, the choroid mode being one of the imaging modes.

16. An optical coherence tomography apparatus according to claim 1, wherein the learned model is obtained from training data in which input data is a new tomographic image obtained by shifting a tomographic image of an eye to be examined in a depth direction of the eye to be examined by a predetermined shifting amount and that includes the shifting amount as ground truth.

17. An optical coherence tomography apparatus according to claim 1, wherein the controlling unit performs exception processing in a case where information on an output from the learned model does not satisfy a determination condition relating to the end of the driving by the driving unit.

18. An optical coherence tomography apparatus that obtains a tomographic image of an eye to be examined by using combined light obtained by combining (a) return light from the eye to be examined irradiated with measurement light and (b) reference light, the optical coherence tomography apparatus comprising:

a driving unit arranged to drive an optical member included in the optical coherence tomography apparatus; and a controlling unit configured to control the driving unit using a driving amount of the driving unit, wherein the driving amount is determined from the obtained tomographic image using a learned model that is obtained from training data in which input data is a new tomographic image obtained by shifting a tomographic image of an eye to be examined in a depth direction of the eye to be examined by a predetermined shifting amount and that includes the shifting amount as ground truth.

19. An optical coherence tomography apparatus according to claim 18, wherein the controlling unit performs exception processing in a case where information on an output from the learned model does not satisfy a determination condition relating to the end of the driving by the driving unit.

20. A control method for an optical coherence tomography apparatus that obtains a tomographic image of an eye to be examined by using combined light obtained by combining (a) return light from the eye to be examined irradiated with measurement light and (b) reference light, the optical coherence tomography apparatus including an optical path length difference changing unit arranged to change an optical path length difference between the measurement light and the reference light and a driving unit arranged to drive the optical path length difference changing unit, the method comprising:

controlling the driving unit using a driving amount of the driving unit, wherein the driving amount is determined using a plurality of values output from a learned model by inputting to the learned model a plurality of tomographic images obtained for different optical path length differences.

21. A non-transitory computer-readable storage medium storing a program for causing, when being executed by a computer, the computer to execute the steps of the control method according to claim 20.

22. An optical coherence tomography apparatus that obtains a tomographic image of an eye to be examined by using combined light obtained by combining (a) return light from the eye to be examined irradiated with measurement light and (b) reference light, the optical coherence tomography apparatus comprising:

an optical path length difference changing unit arranged to change an optical path length difference between the measurement light and the reference light;

a driving unit arranged to drive the optical path length difference changing unit; and a controlling unit configured to control the driving unit using a driving amount of the driving unit, wherein the driving amount is determined from the obtained tomographic image using a learned model obtained by supervised learning using a plurality of training data that includes a plurality of tomographic images and a plurality of values obtained for different optical path length differences.

23. An optical coherence tomography apparatus according to claim 22, wherein the controlling unit performs exception processing in a case where information on an output from the learned model does not satisfy a determination condition relating to the end of the driving by the driving unit.

24. A control method for an optical coherence tomography apparatus that obtains a tomographic image of an eye to be examined by using combined light obtained by combining (a) return light from the eye to be examined irradiated with measurement light and (b) reference light, the optical coherence tomography apparatus including an optical path length difference changing unit arranged to change an optical path length difference between the measurement light and the reference light and a driving unit arranged to drive the optical path length difference changing unit, the method comprising:

controlling the driving unit using a driving amount of the driving unit, wherein the driving amount is determined from the obtained tomographic image using a learned model obtained by supervised learning using a plurality of training data that includes a plurality of tomographic images and a plurality of values obtained for different optical path length differences.

25. A non-transitory computer-readable storage medium storing a program for causing, when being executed by a computer, the computer to execute the steps of the control method according to claim 22.

26. An optical coherence tomography apparatus that obtains a tomographic image of an eye to be examined by using combined light obtained by combining (a) return light from the eye to be examined irradiated with measurement light and (b) reference light and is capable of obtaining a fundus observation image, the optical coherence tomography apparatus comprising:

an optical path length difference changing unit arranged to change an optical path length difference between the measurement light and the reference light;

a driving unit arranged to drive the optical path length difference changing unit; and a controlling unit configured to control the driving unit using a driving amount of the driving unit, wherein the driving amount is determined using a plurality of values output from a learned model by inputting to the learned model a plurality of fundus observation images obtained for different optical path length differences.

27. An optical coherence tomography apparatus according to claim 26, wherein the learned model is a regression model and is obtained by supervised learning using a plurality of training data that includes a plurality of fundus observation images and a plurality of values obtained for different optical path length differences.

28. An optical coherence tomography apparatus according to claim 26, wherein the controlling unit performs exception processing in a case where information on an output from the learned model does not satisfy a determination condition relating to the end of the driving by the driving unit.

* * * * *